United States Patent [19]

Simpkins

[11] Patent Number: 5,843,934
[45] Date of Patent: Dec. 1, 1998

[54] USES OF ESTROGEN COMPOUNDS FOR THE TREATMENT OF DISEASE

[75] Inventor: James W. Simpkins, Gainesville, Fla.

[73] Assignee: University of Florida Research Foundation, Inc., Gainesville, Fla.

[21] Appl. No.: 648,857

[22] Filed: May 16, 1996

Related U.S. Application Data

[63] Continuation-in-part of Ser. No. 149,175, Nov. 5, 1993, abandoned, and a division of Ser. No. 318,042, Oct. 4, 1994, Pat. No. 5,554,601.

[51] Int. Cl.$^6$ .................................................. A61K 31/56
[52] U.S. Cl. ............................................................ 514/182
[58] Field of Search ............................................ 514/182

[56] References Cited

U.S. PATENT DOCUMENTS

| | | | |
|---|---|---|---|
| 4,897,389 | 1/1990 | Aroonsakul | 514/171 |
| 5,393,763 | 2/1995 | Black | 514/333 |
| 5,510,370 | 4/1996 | Hock | 514/443 |
| 5,641,790 | 6/1997 | Draper | 514/333 |
| 5,686,476 | 11/1997 | May | 514/324 |

FOREIGN PATENT DOCUMENTS

| | | |
|---|---|---|
| WO 92/13538 | 8/1992 | WIPO . |
| WO 92/14474 | 9/1992 | WIPO . |
| WO95/10513 | 4/1995 | WIPO . |

OTHER PUBLICATIONS

1955 Wroblewski et al., *Proc. Soc. Exp. Biol. Med.* 90:210–213.
1964 Black et al., *Exp. Cell Research* 35:9–13.
1970 Oldendorf, *Brain Res.* 24:37–46.
1971 Oldendorf, *Am. J. Physiol.* 221:1629–1638.
1975 Fonnum, *J. Neurochem.* 24:407–409.
1976 Kolbe et al., *Biochemistry & Biophysics* 73:378–382.
1976 Keller et al., *Archives of Pharmacology* 294:213–215.
1977 Perez–Polo et al., *Life Sci.* 21:1535–1543.
1980 Luine et al., *Brain Research* 191:273–277.
1982 Barde et al., *EMBO J.* 1:549–553.
1984 Fallon et al., *Science* 224:1107–1109.
1986 Morrison et al., *Prc. Nat'l. Acad. Sci. U.S.A.* 83:7537–7541.
1986 Morse et al., *Experimental Neurology* 94:649–658.
1986 Aizenman et al., *Proc. Nat'l. Acad. Sci. U.S.A.* 83:2263–2266.
1986 Fillet et al., *Psychoneuroendocrinology* 11:337–345.
1987 Morrison et al., *Science* 238:72–75.
1987 Monard, *Biochem. Pharmacol.* 36:1389–1392.
1987 Thoenen et al., *Rev. Physiol. Biochem. Pharmacol.* 109:145–178.
1987 Whittemore et al., *J. Neurosci.* 7:244–251.
1987 Baskin et al., *Ann. Rev. Physiol.* 49:335–347.
1988 Derynck, *Cell* 54:161–170.
1988 Rosenberg et al., *Science* 242:1575–1578.
1988 Walicke, *J. Neurosci.* 8:2618–2627.
1988 Mouton et al., *Brain Research* 444:104–108.
1989 Stockli et al., *Nature* 342:920–923.
1989 Yamamori et al., *Science* 246:1412–1416.
1989 Oltersdorf et al., *Nature* 341:144–147.
1989 Whitson et al., *Science* 243:1488–1490.
1989 Hama et al., *Neurosci. Lett.* 104:340–344.
1989 Hefti et al., *Neurobiol. Aging* 10:515–533.
1989 Lin et al., *Science* 246:1023–1025.
1989 Honjo et al., *Steroid Biochemistry* 34:521–524.
1989 Gall et al., *Science* 245:758–761.
1990 Kovesdi et al., *Biochem. Biophys. Res. Commun.* 172:850–854.
1990 Kamegai, *Neuron* 2:429–436.
1990 Hohn et al., *Nature* 344:339–341.
1990 Fallon et al., *Growth Factors* 2:241–250.
1990 Spranger et al., *Eur. J. Neurosci.* 2:69–76.
1990 Maisonpierre et al., *Neuron* 5:501–509.
1990 Ernfors et al., *Neuron* 5:511–526.
1990 Rosenthal et al., *Neuron* 4:767–773.
1991 Hallbrook et al., *Neuron* 6:845–858.
1991 Berkemeier et al., *Neuron* 7:857–866.
1992 Woolley et al. *Journal of Neuroscience* 12:2549–2554.
1993 Gibbs et al., *Society for Neuroscience Abstracts* 19:5.
1987 Wright et al., *Int. J. Dev. Neuroscience* 5:305–311.
1988 Jones, *Metabolic Brain Disease* 3:1–18.
1992 Mizoguchi et al., *Neuroscience Letters* 138:157–160.
1992 Honjo et al., *J. Steroid Biochem. Molec. Biol.* 41:633–635.
1993 Emerson et al., *Brain Research* 608:95–100.
1996 Draper, Michael W., et al, "A Controlled Trial of Raloxifene (LY139481) HCl: Impact on Bone Turnover and Serum Lipid Profile in Healthy Postmenopausal Women", *Journal of bone and Mineral Research;* vol. 11.
1994 Evans, Glenda, et al, "The Effects of Raloxifene on Tibia Histomorphometry in Ovariectomized Rats", *Endocrinology;* 1345–2283.
1994 Sato, Masahiko, et al, "Dual–Energy X–ray Absorpitiometry of Raloxifene Effects on the Lumbar Vertebrae and Femora of Ovariectomized Rats", *Journal of Bone and Mineral Research,* vol. 9, No. 5.
1995 Sato, Masahiko, et al, "Longitudinal and Cross–Section Analysis of Raloxifene Effect on Tibiae from Ovariectomized Aged Rats", *The Journal of Pharmacology and Experimental Therapeutics,* 272:1252–1259.
Chemical Abstracts (115:214850) Miura et al. (1991) See the Enclosed Abstract.

*Primary Examiner*—Kevin E. Weddington
*Attorney, Agent, or Firm*—Bromberg & Sunstein LLP

[57] ABSTRACT

A method is provided for conferring a cytoprotective effect on a population of cells in a male of female subject which includes providing an estrogen compound having insubstantial sex related activity in a pharmaceutical formulation and administering the formulation in an effective dose to a population of cells to confer cytoprotection. The method further includes administering the estrogen compound so as to confer a cytoprotective effect in a subject so as to retard adverse effects of osteoporosis in a male or female subject.

6 Claims, 10 Drawing Sheets

| R₁ AND/OR R₂ SUBSTITUTIONS ||
|---|---|
| NAME | STRUCTURE |
| HYDROXYL | $-OH$ |
| METHYL | $-CH_3$ |
| METHYL ESTER | $-OCH_3$ |
| ACETATE | $O-\underset{\underset{O}{\|}}{C}-CH_3$ |
| ETHYL ETHER | $O-CH_2-CH_3$ |
| 3, 3, (OR 17, 17) DIMETHYL KETAL | $\begin{array}{l} -OCH_3 \\ -OCH_3 \end{array}$ |
| ETHYNYL-α | $\begin{array}{l} C\equiv CH \\ OH \end{array}$ |
| BENZOATE | $O-C\overset{O}{\diagdown}\text{–}\bigcirc$ |
| BENZYL ETHER | $OCH_2-\bigcirc$ |
| GLUCURONIDE | $C_6H_8O_6$ |
| SULFATE, SODIUM SALT | $OSO_3Na$ |
| OXIDE | $=O$ |
| VALERATE | $-C_5H_8O$ |
| CYCLOPENTYLPROPIONATE | $-O-\overset{O}{\overset{\|}{C}}-(CH_2)_2-\triangleleft$ |
| PROPIONATE | $-O-\overset{O}{\overset{\|}{C}}-(CH_2)_2$ |
| HEMISUCCINATE | $-C_4H_4O_3$ |
| PALMITATE | $-C_{16}H_{32}O_2$ |

FIG.9A

USES OF ESTROGEN COMPOUNDS FOR THE TREATMENT OF DISEASE

CROSS REFERENCE TO RELATED APPLICATIONS

This is a continuation-in-part of U.S. application Ser. No. 08/149,175, filed on Nov. 5, 1993 now abandoned and a divisional of U.S. application Ser. No. 08/318,042 filed Oct. 4, 1994 now U.S. Pat. No. 5,554,601.

TECHNICAL FIELD

The present invention relates to methods for protecting cells in the central nervous system of subjects from cell death and for stimulating neuronal survival through enhanced growth factor production.

BACKGROUND OF THE INVENTION

Neurodegenerative diseases have a major impact on society. For example, approximately 3 to 4 million Americans are afflicted with a chronic neurodegenerative disease known as Alzheimer's disease. Other examples of chronic neurodegenerative diseases include diabetic peripheral neuropathy, multiple sclerosis, amyotrophic lateral sclerosis, Huntingdon's disease and Parkinson's disease. Not all neurodegenerative diseases are chronic. Some acute neurodegenerative diseases include stroke, schizophrenia, and epilepsy as well as hypoglycemia and trauma resulting in injury of the brain, peripheral nerves or spinal cord. There is a need for improved therapeutic agents and methods for reversing or retarding neuronal damage associated with each of these conditions.

Neurodegenerative diseases and aging are characterized by a wide range of symptoms which vary in severity and range from individual to individual. For example, Alzheimer's disease is characterized by symptoms such as depression, aggression, impairment in short-term memory, impairment in intellectual ability, agitation, irritability and restlessness. Since estrogen becomes deficient in postmenopausal women, and since estrogen is believed to affect mood, some studies have been undertaken to assess the relief of behavioral symptoms associated with Alzheimer's disease. Unfortunately, those clinical trials that have been performed to establish the beneficial effect of estrogen on Alzheimer's disease have concluded that no statistically significant improvements in the disease course or symptoms resulted from the treatment. Fillet et al. 1986, *Psychoneuroendocrinology* 11:337–345; Honjo et al. 1989, *Steroid Biochemistry* 34:521–524. In one study where only 1 female and 1 male patient were studied and no statistics were available, a rapid reduction in symptoms of senile dementia was observed when estrogen was administered to the female patient in a cocktail of drugs together with chorionic gonadotrophin, a vasodilator and a non-steroidal anti-inflammatory agent after a period as short as one week (Aroonsakul 1990, U.S. Pat. No. 4,897,389). There is a need for a better understanding of the underlying process of neurodegeneration such that improved treatment protocols and effective drugs may be designed that are effective at treating the disease itself so as to bring about a longterm meaningful reversal of symptoms.

A common feature of neurodegenerative disorders and the process of aging in animals is the progressive cell damage of neurons within the central nervous system (CNS) leading to loss of neuronal activity and cell death. This loss of activity has been correlated with adverse behavioral symptoms including memory loss and cognitive deficits. Therapeutic agents that have been developed to retard loss of neuronal activity either have toxic side effects or are prevented from reaching their target site because of their inability to cross the blood-brain barrier. The blood-brain barrier is a complex of morphological and enzymatic components that retards the passage of both large and charged small molecules thereby limiting access to cells of the brain. There is a need for novel therapeutic agents that are readily transported across the blood-brain barrier as well as for novel methods of treatment of neurodegenerative disorders that directly target the damaged site and are non-toxic.

Traditional methods of treating neurological symptoms focus on; modifying the electrical impulse itself as it moves between and along neurons; or modifying the release or degradation of neurotransmitters. It is now recognized that neuronal cell density has an important impact on function. In various pathological conditions, loss of cell density has been observed resulting from accelerated neuronal cell death. The pattern of degeneration of neurons typically originates from the nerve terminals and progresses "backward" toward the cell body (retrograde degeneration). In several systems, lesioning of certain brain regions results in compensatory sprouting of axons. This plasticity of neurons is attributed at least in part to the presence of trophic growth factors.

These findings have spurred efforts to identify therapeutic agents that compensate for cell loss by stimulating sprouting of dendrites and axons of remaining cells so as to improve the structural integrity of the damaged region. However, the optimal density of neurons and neuronal extensions is a delicate balance between deficiency and excess, a balance that varies with the environment of the cells. This balance can be disrupted when therapeutic agents act on normal or inappropriate tissue. There is a need therefore to target therapeutic agents at a therapeutic dose specifically to those regions where they are required, or, alternatively, to identify agents that have a natural specificity for the target site only.

To date, there are no safe and effective methods for treating loss of neuronal activity. However, considerable attention has recently been focused on naturally occurring proteins, collectively called neurotrophic factors (see Table I), that promote growth and maintenance of cells of the central nervous system (CNS) and sympathetic and sensory neurons of the peripheral nervous system. In particular, the administration of nerve growth factor (NGF), a protein which is normally transported retrogradely in the intact brain from the hippocampus to the septal cholinergic cell bodies as well as from the cortex to the nucleus basalis, provides trophic support to cholinergic neurons and has been shown in animal models to have utility in reducing the effects of neurodegeneration due to trauma, disease or aging. The septum and the nucleus basalis are part of a region of the brain known as the basal forebrain. The effectiveness of administering NGF in response to damage is supported by experiments that demonstrate that cholinergic neurons in the medial septum can be protected from retrograde degeneration by chronic infusion of exogenous NGF (Rosenberg et al. 1988, *Science* 242:1575–1578). Indeed, infusion of NGF has been shown to significantly attenuate retrograde degeneration of cholinergic neurons after transection of their connections in the fimbria (the septo-hippocampal pathway).

One of the major problems confronting the use of NGF as a therapeutic agent is finding an appropriate method of increasing the levels of NGF at the appropriate target site. NGF is a large molecule and as such cannot normally pass across the blood-brain barrier and therefore has very limited access to the cells of the brain. Invasive methods are commonly used to place externally administered NGF within the brain. These methods are not sufficient to target NGF specifically to those cells where it is required. Nonlocalized targeting not only decreases the amount of protein available at the target site but also results in stimulation of growth of neurons at inappropriate sites resulting in potential harmful effects for the subject.

Another disadvantage of administering NGF as a therapeutic agent is that of induction of an immunological response to this protein. There is a need therefore for a compound that does not in itself cause an immune response but could stimulate the production of endogenous NGF.

Current methods for administering nerve growth factor across the blood-brain barrier include: polymeric implants, osmotic minipumps, cell therapy using genetically engineered autologous or heterologous cells secreting NGF for implantation into the brain, and methods of increasing the permeability of the blood-brain barrier thereby allowing diffusion of these molecules to cells in the brain. Where exogenous NGF is used, a relatively large amount of relatively costly recombinant protein is required.

Rather than these aforestated solutions to delivery of proteins, it would be desirable to: avoid invasive techniques; to control the amount and the site of delivery of neurotrophic proteins to sites where they are most needed thereby minimizing toxic side effects; and to minimize the health care costs of treatment.

An additional approach to treating neurological symptoms has followed the observation that certain amino acids (glutamic acid and aspartic acid) act as excitatory neurotransmitters that bind the N-methyl D-aspartate (NMDA) receptor. Excess release of these amino acids (EAA) causes overstimulation of the neurons in neurodegenerative diseases as well as in conditions of hypoglycemia or trauma, resulting in neuronal loss and behavioral dysfunctions. NMDA is a potent and toxic analogue of glutamate which has been shown in animal studies to mediate much of the neuronal death associated with head trauma, hypoglycemia, anoxia, hypoxia and other conditions, and compromises the flow of blood, oxygen or glucose to the central nervous system.

A number of synthetic compounds that act as antagonists of the receptor have been described and tested in animal models. The possibility that these compounds are toxic in humans remains unresolved. Despite many years of clinical research, these antagonists are not as yet available as therapeutic products for treating patients.

For the foregoing reasons there is a need for methods of protecting neurons from accelerated cell death caused by trauma or disease or by the aging process or by combinations of these factors. There is also a need for methods that stimulate the production of neurotrophic growth factors using small molecules that are capable of crossing the blood-brain barrier and that have minimal side effects.

SUMMARY

A preferred embodiment of the invention is directed toward a method of protecting a population of nerve cells from death that includes administering to a nerve cell population in an animal subject an effective dosage of an estrogen compound sufficient to cause the nerve cell population to be protected from progressive cell damage leading to the death of the cells otherwise occurring without any intervention, wherein the estrogen has a general structure: a tautomer thereof, or a pharmaceutically acceptable salt thereof

BRIEF DESCRIPTION OF THE DRAWINGS

These and other features will become better understood with regard to the following description, appended claims and accompanying drawings where:

DETAILED DESCRIPTION OF THE INVENTION

The present invention is directed toward methods for protecting a population of nerve cells in a subject from death and toward stimulating neurotrophic factors for protecting cells from cell death in an animal subject.

Figure 9B:
FIG. 9 shows examples of molecular structures for α and β estradiols capable of acting as neuroprotectants.
Figure 9B:
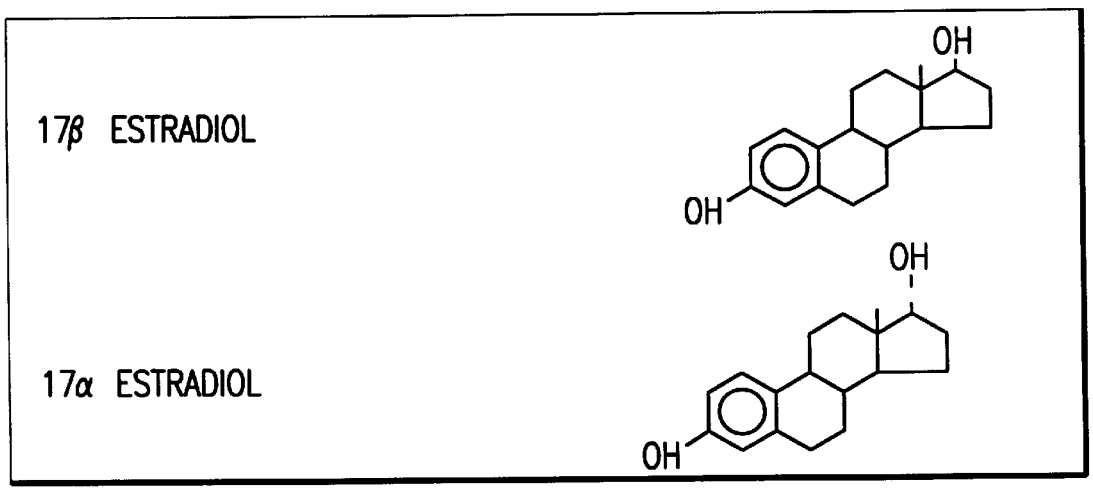

An "estrogen compound" is defined here and in the claims as any of the structures described in the 11th edition of "Steroids" from Steraloids Inc., Wilton N. H., here incorporated by reference. Included in this definition are non-steroidal estrogens described in the aforementioned reference. Other estrogen compounds included in this definition are estrogen derivatives, estrogen metabolites and estrogen precursors as well as those molecules capable of binding cell associated estrogen receptor as well as other molecules where the result of binding specifically triggers a characterized estrogen effect. Also included are mixtures of more than 1 estrogen, where examples of such mixtures are provided in Table II below. Examples of α estrogen structures having utility either alone or in combination with other agents are provided in FIG. 9.

β estrogen is the β isomer of estrogen compounds. α estrogen is the α isomer of estrogen components. The term "estradiol" is either α or β estradiol unless specifically identified.

The term "E$_2$" is synonymous with β-estradiol 17β-estradiol and β-E$_2$. αE$_2$, α-E$_2$, and α-estradiol is the α isomer of β-E$_2$ estradiol.

An "animal subject" is defined here and in the claims as a higher organism including humans having neurons subjected to forces that result in progressive cell damage and cell death.

"Neurotrophic growth factors" are defined here and in the claims as endogenous soluble proteins regulating survival, growth, morphological plasticity or synthesis of proteins for differentiated function of neurons.

"Neurodegenerative disorder" is defined here and in the claims as a disorder in which progressive loss of neurons occurs either in the peripheral nervous system or in the central nervous system. Examples of neurodegenerative disorders include: chronic neurodegenerative diseases such as Alzheimer's disease, Parkinson's disease, Huntington's chorea, diabetic peripheral neuropathy, multiple sclerosis, amyotrophic lateral sclerosis; aging; and acute neurodegenerative disorders including: stroke, traumatic brain injury, schizophrenia, peripheral nerve damage, hypoglycemia, spinal cord injury, epilepsy, and anoxia and hypoxia.

These examples are not meant to be comprehensive but serve merely as an illustration of the term "neurodegenerative disorder."

TABLE I

List of Characterized Proteins
Exhibiting Neurotrophic Activities

| Growth Factor | References* |
|---|---|
| Proteins initially characterized as neuratrophic factors: | |
| Nerve growth factor (NGF) | Thoenen et al., 1987 |
| Brain-derived neurotrophic factor (BDNF) | Whittemore et al., 1987<br>Hafti et al., 1989<br>Barde at al., 1982<br>Lei?? et al., 1989 |
| Neurotrophin-3 (NT-3) | Ernfors et al., 1990<br>Hohn et al., 1990<br>Maisonpierre et al., 1990<br>Rosenthal et al., 1990 |
| Neurotrophin-4 (NT-4) | Hallbrook et al., 1991 |
| Neurotrophin-5 (NT-5) | Berkemeier et al., 1991 |
| Ciliary neurotrophic factor (CNTF) | Lin et al., 1989<br>Stockli et al., 1989 |
| Heparin-binding neurotrophic factor (HBNF) | Kovesdi et al., 1990 |
| Growth factors with neurotrophic activity: | |
| Basic fibroblast growth factor (bFGF) | Morrison et al., 1986<br>Walicke, 1988 |
| Acidic fibroblast growth factor (aFGF) | Walicke, 1988 |
| Insulin-like growth factors (IGF's), insulin | Aizenman et al., 1986<br>Baskin et al., 1987 |
| Epidermal growth factor (EGF) | Fallon et al., 1984<br>Morrison et al., 1987 |
| Transforming growth factor α (TGFα) | Derynck, 1988<br>Fallon et al., 1990 |
| Interleukin 1 | Spranger et al., 1990 |
| Interleukin 3 | Kamegai, 1990 |
| Interleukin 6 | Hama et al., 1989 |
| Protease ?? I and II | Monard, 1987<br>Olmsdorf et al., 1989<br>Whitson et al., 1989 |
| Cholinergic neuronal differentiation factor | Yamamori et al., 1989 |

*References given refer to recent reviews or recent key publications.

TABLE II

Commercial Estrogen Preparations

1. Estrone Aqueous Suspensions Usual dasage IM, 0.1 to 0.5 mg, 2 to 3 times weekly.
2. Estradiol Estrase: 1 to 2 mg PO, daily for three weeks; one week off.
3. Estradiol Conjugates in Oil.
   a. Estradiol-cypionate 1 to 5 mg IM; every 3 to 4 weeks-more than 20 preparations.
   b. Estradiol-valerate 10 to 20 mg IM; every 4 weeks - more than 30 preparations.
4. Oral estrogen preparations 50 to 65% estrone sulfate and 20 to 35% equilin sulfate.
   a. Premarin 0.3 to 2.5 mg PO daily for 3 weeks; one week
   b. Estrocon 0.625 to 2.5 mg PO daily for 3 weeks; one week off.
   c. Progens 0.625 to 2.5 mg PO daily for 3 weeks; one week off.
   d. Many others 0.625 to 2.5 mg PO daily for 3 weeks; one week off.
5. Oral Esterified Estrogens 75 to 85% estrone sulfate and 6 to 15% equilin sulfate.
   a. Estratab 0.3 to 2.5 mg PO daily for three weeks; one week off.
   b. Menest 0.3 to 2.5 mg PO daily for three weeks; one week off.
6. Estropipate Piperazine Estrone Sulfate.
   a. Ogen 0.625 to 5 mg PO daily for 3 weeks: one week off.
7. Ethinyl Estradiol.
   a. Estinyl 0.02 to 0.5 mg PO daily for three weeks; one week off.
   b. Feminone 0.05 mg PO daily for three weeks; one week off.
8. Quinestrol a fat stored, slow release form of ethinyl estradiol.
   a. Estrovis 100 μg PO daily for 7 days; 100, ug weekly thereafter.
9. Diethylstilbestrol (0.2 to 0.5 mg PO daily for three weeks; one week off.
10. Chlorotrianisene Tace; 12 to 25 mg PO daily for three weeks; on week off.
11. Oral Estrogen-Antianxiety Agent Combinations Oral.
    a. Milprem-200 or -400 (Conjugated estrogens and meprobamate).
    b. PMB 20 or 400 (Conjugated estrogens and meprobamate).
    c. Menrium 5-2, 5-4, or 10-4 esterified estrogens and chlordiazepoxide.
12. Estrogen and Androgen Combinations IM in Oil.
    a. 13 preparations with 2 mg estradiol cypionate and 50 mg testosterone cypionate.
    b. 12 preparations with 4 mg estradiol valerate and 90 mg testosterone enanthate.
    c. 4 preparations with 8 mg estradiol valerate and 180 mg testosterone enanthate.

TABLE II-continued

Commercial Estrogen Preparations d. 6 preparations with various combinations of other estrogens and androgens.

Properties of Estrogen.

Estrogen occurs in at least two isomeric forms, including α estrogen and α estrogen. β estrogens are pleotrophic molecule with many biological activities. Clinical uses include treatment of osteoporosis, symptoms of menopause and fertility control. In embodiments of the invention, β estrogen has also been shown to protect a subject against neuronal loss.

In comparison to β estrogen, α estrogen is typically believed to be at least 100–1000 times less potent in estrogenic activity. Numerous examples have been reported in the literature that show that the biological effects of β estrogen are not shared by the α isomer. In fact, in the art, α estrogen is typically used as a negative control for β estradiol.

We have shown for the first time that α estrogen has a comparable activity to that of β estrogen for neuroprotection. The novel activity identified for α estrogen presents a number of advantages in the treatment of neurodegenerative diseases, trauma and aging. These advantages arise in situations which require treatment of males where the development of female traits is to be avoided and the treatment of females where the subject has increased susceptibility to endometrial, breast and cervical cancer.

In an embodiment of the invention, a novel use for estrogen has been identified, namely to cause arrest and/or reversal of progressive degeneration of neurons. The degenerative process ultimately leads to behavioral defects that accompany reduction in observed neuronal density. According to this invention, improvements in cognition, memory and other behavioral symptoms occur in subjects suffering from neurodegenerative disorders caused individually by disease, trauma or aging or a combination of these factors following administration of estrogen. Also according to this invention is an arrest in progression of a neurodegenerative disease such as by intervention and/or prevention of neuronal loss the patient will not develop or manifest a further decline in disease course. Evidence for this effect is shown in the accompanying examples and is correlated with biochemical effects identified both in vivo and in vitro.

In Example 1, in vitro studies have demonstrated cytoprotective properties of estrogen where comparatively low concentrations of $\alpha$-$E_2$ and $\beta$-$E_2$ enhance viability in neuronal cells. In a further embodiment of the invention, pretreatment of cells with $\beta$-$E_2$ has been shown to protect cells from death caused by glucose reduction or deprivation, a condition called hypoglycemia. Post-treatment with $E_2$ can rescue cells from the effects of hypoglycemia in a manner that dissipates with increasing length of hypoglycemia (Example 2).

These examples demonstrate that both α and β estradiol at physiologically relevant doses exert a cytoprotective effect on both glial and neuroblastoma cells lines in vitro and that this cytoprotective effect can be distinguished from a mitogenic action. While not wishing to be bound by theory, we hypothesize that estrogen exerts a direct protective effect on neuronal cells.

In vivo studies described in Examples 3–6 have shown that estrogen can reverse an impairment in non-spatial learning. This impairment is correlated with a time dependent decline in choline acetyl transferase (ChAT) in both the frontal cortex and the hippocampus which is attenuated in animals treated with estradiol. The ChAT-containing nerve terminals in these two brain regions have cell bodies located in the basal forebrain. In Example 3, rats have shown improvements in behavioral performances as determined by the active avoidance test following the addition of estrogen to estrogen deficient ovariectomized animals. Collectively, these data provide a method of treating subjects through the modulation of basal forebrain cholinergic function by means of treating with estrogen so as to reduce loss of learning and memory associated with neuronal damage.

Examples 1–6 demonstrate a number of different pathways through which estrogen compounds exert a cytoprotective effect on cells in the CNS. These include protection against hypoglycemia (Examples 2a, 2b, and 6) and protection from overstimulation of EAA (Examples 2c and 5), as well as by the stimulation of neurotrophic growth factor production (Examples 4a and 4b).

Example 4a describes experiments demonstrating the increase in brain derived neurotrophic factor (BDNF) determined by increased levels of BDNF mRNA while Example 4b describes the stimulation of nerve growth factor production determined by increased levels of NGF mRNA. A further cytoprotective effect of estrogen has been demonstrated by the amelioration of the toxic effects of overstimulation of excitatory amino acid (EAA) receptors (Examples 2c and 5). Overstimulation of the EAA receptors has been identified as characteristic of a number of neurodegenerative disorders including epilepsy. In a further embodiment of the invention, the estrogen compounds ameliorate the toxic effects of hypoglycemia that is a further cause of progressive cell damage leading to cell death (Examples 2a, 2b, and 6).

While not wishing to be bound by theory, it is suggested that estrogen compounds act on a fundamental process that impacts cell viability and cell response to adverse conditions that result in damage and death and that this process underlies the observed phenomena. An example of such a mechanism includes the regulation of glucose to cells.

These observations contrast with observations of the prior art. Although estrogen has been identified as having utility in treating adverse behavioral symptoms that accompany fluctuations in hormones associated with menopause in aging women, the biochemical basis for these effects has never been determined. As such, the treatment of behavioral effects with estrogen in human subjects has been restricted to the treatment of menopause in women that demonstrate signs of deficiency in estrogen and use in prevention of the sequelae of menopause, namely osteoporosis, corrected by replacement therapy of estrogen.

The human clinical studies do however demonstrate that externally administered estrogen is non toxic. In addition, these studies demonstrate that estrogen administered intramuscularly subsequently reaches the brain as inferred by the behavioral effects of the treatment and as predicted from the structure of the molecule.

Although clinical studies by Sherwin 1988, *Psychoneuroendocrinology* 13:345–357, and Sherwin and Phillips 1990, *Annals of the New York Academy of Sciences* 592:474–5, have shown a general mood enhancing effect in oophorectomized women following intramuscularly administration of estrogen at doses of 10 mg, the mechanism by which this effect occurred is unclear.

Biochemical studies on the action of estrogen on cells of the CNS either in vivo or in vitro has resulted in conflicting reports. A number of studies have shown that estradiol has an effect on the plasticity of neurons. Morse et al. 1986, *Experimental Neurology* 94:649–658, reported that an estrogen derivative enhances sprouting of commissural-associational afferent fibers in the hippocampal dentate gyrus following entorhinal cortex lesions. Additionally, cyclic changes in synaptic density in the CA1 of the hippocampus were shown to be related to circulating $E_2$ levels (Woolley et al. 1992, *Journal of Neuroscience* 12:2549–2554) and these changes could be mimicked with exogenous $E_2$ administration (Woolley et al. 1992). Indeed, it has further been shown that ovariectomy reduces and $E_2$ replacement normalizes high affinity choline uptake (HACU) in the frontal cortex of rats.

Additionally, Gibbs et al. 1993 (*Society for Neuroscience Abstracts* 19:5) have reported upregulation of choline acetyltransferase (ChAT) levels following estradiol treatment in the medial septum after 2 days and 2 weeks of treatment although no effect was observed after 1 week using in situ hybridization of CHAT mRNA. Luine et al. 1980, *Brain Research* 191:273–277, reported increased ChAT levels in the preoptic and hypothalamic regions of the rat brain in response to estradiol treatment.

In an embodiment of the invention, administration of estrogen in a physiological dose results in the reversal of impairment of non-spatial learning in female rats that have been ovariectomized (OVX). These behavioral effects of short-term OVX and $E_2$-replacement are correlated with biochemical changes in the hippocampus and the frontal cortex of the brain; in particular, a reduction and increase in high affinity choline uptake (HACU) in OVX and $E_2$-pellet treated rats, respectively. Short-term $E_2$-replacement also had a positive effect on choline acetyltransferase activity (ChAT) in the hippocampus, but not in the frontal cortex. Long-term $E_2$ replacement appeared to prevent the time-dependent decline of CHAT in the frontal cortex and to attenuate CHAT activity decline in the hippocampus. Collectively, these data show that estrogen has a cytoprotective effect on cells in the CNS and that the estrogen environment of adult female rats influences learning and the activity of basal forebrain cholinergic neurons and also demonstrate the importance of estrogens in the maintenance and proper function of basal forebrain cholinergic neurons in the female rat.

In 1977, Perez-Polo et al. (*Life Sci.* 21:1535–1543) published a paper entitled "Steroid Induction of Nerve Growth Factor Synthesis in Cell Culture". Although the title indicates a positive effect of steroids on the production of NGF by glial cells in vitro, closer inspection of the paper revealed the opposite. By using non-specific polyclonal antibodies, increased levels of a high molecular weight molecule was identified in response to high levels of estrogen whereas there was no increase in the amount of a low molecular weight (MW) fraction now known to contain β NGF and similarly recognized by the antibody preparation. The doses of estrogen used in the experiment were 5,500 times higher then physiological levels. The levels of the low MW fraction attributed to NGF and secreted into the media were found to be 1000-fold higher than predicted for NGF production using current methods. No further work was carried out by these investigators or others to determine in vivo effects of estrogen on NGF production. Subsequent in vivo studies by Gibbs et al. 1993 reported that steroids (17-β estradiol) caused decreased levels of NGF mRNA in the hippocampus followed by decreased levels in the medial septum and the diagonal band of Broca.

Contrary to the above report, an embodiment of the invention describes how estradiol stimulates the production of neurotrophic growth factor mRNA. For the first time, an estrogen compound has been described that not only has ready access to brain tissue across the blood-brain barrier but can stimulate the availability of growth factor where it is most needed so as to reverse and offset the effects of neurodegeneration.

In a preferred embodiment of the invention, novel properties have been identified for estrogen compounds that provide for the first time a method of using estrogen to arrest and/or reverse progression of neurodegenerative disorders rather than merely treating the symptoms of the disease.

In a preferred embodiment, both stereoisomers of estradiol, 17-β-estradiol and 17-α-estradiol have been found effective in reversing neurodegeneration.

In a preferred embodiment, estradiol is administered to rats and also to humans at concentrations sufficient to exert neuroprotective effects in the CNS. These doses vary according to interperson variability, the route of administration and the estrogen formulation used. For example, in rats, estradiol is administered subcutaneously by means of a silastic tube to achieve plasma levels of about 50 pg/ml. In humans, 0.2–10 mg or more specifically 1–2 mg of orally administered estrase (estradiol) given daily is commonly administered to patients suffering from post menopausal syndrome. These levels are also expected to be effective in treating neurodegenerative disorders in human subjects.

The recommended route of administration of the estrogen compound includes oral, intramuscular, transdermal, buccal, intravenous and subcutaneous. Methods of administering estrogen may be by dose or by controlled release vehicles.

Administration of estrogen may include the use of a single estrogen compound or a mixture of estrogens.

The protection of cholinergic neurons from severe degeneration is an important aspect of treatment for patients with acute or chronic neurodegenerative disorders, an example of chronic disease being Alzheimer's disease. For Alzheimer's patients, estrogen replacement or supplementation may be of significant therapeutic use. Other diseases for which estrogen treatment may be effective include Parkinson's disease, Huntington's disease, AIDS Dementia, Wernicke-Korsakoff's related dementia (alcohol induced dementia), age related dementia, age associated memory impairment, brain cell loss due to any of the following; head trauma, stroke, hypoglycemia, ischemia, anoxia, hypoxia, cerebral edema, arteriosclerosis, hematoma and epilepsy; spinal cord cell loss due to any of the conditions listed under brain cell loss; and peripheral neuropathy. Because of its cytoprotective properties, it is suggested that one pathway of action for estrogen is the inhibition of apoptosis.

EXAMPLES

Example 1a

In Vitro Studies Demonstrate Increased Viability of Nerve Cells in the Presence of an Estrogen Compound where Estrogen Exerts a Cell Protective Effect.

Experimental design. A neuroblastoma (SK-N-SH) cell line was obtained from American Type Culture Collection (ATCC) (Rockville, Md.). Culture conditions have been described previously (Keller et al. 1976, Kolbe et al. 1976). All experiments were accomplished in cells that were in passage number 3-6. Each experiment was divided into three treatment groups: Group 1 was RPMI media supplemented with 10% fetal bovine serum (FBS), group 2 was RPMI media without the FBS (serum free group) and group 3 was serum free RPMI media supplemented with 544 pg $E_2$/ml ($E_2$ provided by Steraloids, Inc., Wilton, N.H.), greatly in excess of the 16 pg/ml of estrogen normally found in FBS. $E_2$ was initially dissolved in 100 μl absolute ethanol and then diluted with media. Media for the other two groups were similarly prepared with the addition 100 μl absolute ethanol with the media. Media was changed at 48 h into the experiment to maintain the normal schedule of nutrient replenishment.

The rate of growth of the population of cells in each experimental group was measured.

Quantification of cell viability. Cell viability was assessed using the trypan blue dye exclusion method of Black et al. 1964, *Exp. Cell Research* 35:9–13. For each aliquot, two separate counts of total cells and dead cells were made. Live cell number was determined from the difference between total and dead cell number. An important limitation of the trypan blue method of staining is its time dependence. Therefore, care was taken to standardize time between resuspension of the cells, addition of the dye and actual counting on the hemacytometer.

Analysis of data. All data are presented as mean ±SEM after correcting for the dilution factor allowing the data to be expressed as the number of cells per ml. Data were analyzed by an analysis of variance followed by Scheffe's F test. The criterion for significance was p <0.05.

The mitosis ratio was calculated by dividing dead cells (number cells/ml) over total cells (number cells/ml). This index provides a means of distinguishing between the mitotic and the cytoprotective effects of the treatments used in the experimental design. The ratio of dead/total cells was used to differentiate mitotic from cytoprotective effects of $E_2$ in culture.

Experimental results. The ratio of dead to total cells increased by 2 to 3-fold with the removal of FBS from the culture media (Table III). The addition of $E_2$ prevented this serum removal effect and produced ratios similar to those observed in the FBS group at each sample time. Through 48 h, the ratio of dead to live cells remained constant for $E_2$-treated cells, but nearly doubled for serum free cells. By 96 h, the ratio increased in all three groups, indicating the diminishing cytoprotective effect with time.

Although the total SK-N-SH cell number in the FBS group was approximately double that seen with $E_2$ treated cells at both 24 and 48 hours, the fraction of live cells was similar. However, $E_2$-treated SK-N-SH cells did not show the exponential growth pattern seen for cells grown in FBS. The ratio of dead to total SK-N-SH treated cells increased in all three groups with time (Table III). However, at each sampling time, this ratio was similar and markedly lower in both $E_2$ and FBS groups than under serum free conditions.

TABLE III

Dead/Total Cell Ratio for SK-N-SH Cultures

| Time | Treatment | Sample Size (# Flasks) | Ratio (mean ± sem) | Total Cells (×10⁴/ml) | Visble Cells (×10⁴/ml) | Dead Cells (×10⁴/ml) |
|---|---|---|---|---|---|---|
| 24 hrs. | Serum Free | 6 | 0.30 ± 0.03# | 19 ± 2# | 13 ± 4# | 6 ± 1 |
| 24 hrs. | $E_2$ (544 pg/ml) | 6 | 0.16 ± 0.04 | 31 ± 5 | 26 ± 5 | 4 ± 1 |
| 24 hrs. | FBS | 6 | 0.15 ± 0.03 | 34 ± 3 | 29 ± 3 | 5 ± 1 |
| 48 hrs. | Serum Free | 6 | 0.53 ± 0.07# | 21 ± 3# | 11 ± 2# | 11 ± 2 |
| 48 hrs. | $E_2$ (544 pg/ml) | 6 | 0.21 ± 0.05 | 41 ± 9 | 34 ± 9 | 7 ± 2 |
| 48 hrs. | FBS | 6 | 0.14 ± 0.06 | 52 ± 7 | 46 ± 8 | 6 ± 2 |
| 96 hrs. | Serum Free | 5 | 0.62 ± 0.12# | 8 ± 2# | 4 ± 2# | 4 ± 1 |
| 96 hrs. | $E_2$ (544 pg/ml) | 5 | 0.38 ± 0.06* | 22 ± 4* | 14 ± 2* | 8 ± 2 |
| 96 hrs. | FBS | 5 | 0.22 ± 0.04 | 50 ± 8 | 40 ± 8 | 10 ± 1 | p ≤ 0.05 vs both $E_2$ and FBS groups.
*p ≤ 0.05 vs both serum fres and FBS groups.

The growth pattern of neuroblastoma cells in FBS-supplemented media revealed a doubling time of 6 to 9 days. A decrease in total number of cells with a corresponding increase in the fraction of dead cells was observed under serum free conditions across the five day evaluation.

Collectively, these data demonstrate that the enhanced total and live cell number observed results from a cytoprotective, rather than mitotic, effect of $E_2$ under specific in vitro conditions employed.

Example 1b.

In Vitro Studies Demonstrate Increased Viability of Nerve Cells in the Presence of an Estrogen Compound where α-Estrogen Exerts a Cell Protective Effect.

Experimental design. SK-N-SH cells were backcultured with 2 ml 0.02% EDTA (Sigma Chemical Corporation, St. Louis, Mo.), incubated for thirty minutes at 37° C. and resuspended at a density of 1×10⁵ cells per ml as follows. Each experiment had three treatment groups: Group 1 was RPMI media supplemented with 10% FBS (FBS group), group 2 was RPMI media without the FBS (serum free group) and group 3 was serum free RPMI media supplemented with 544 pg/ml 17-α-$E_2$ pg/ml ((α-$E_2$ group) (Steraloids, Inc., Wilton, N.H.). Treatment media were made the day of the experiment. α-$E_2$ was initially dissolved in 100 μl absolute ethanol and then diluted with media. Media for the other two groups was similarly prepared with the addition and dilution of 100 ml absolute ethanol. The FBS has been assayed for β-$E_2$ determining concentrations of about 16 pg/ml. The RPMI 1640 media had undetectable β-$E_2$ levels. However, neither FBS nor media has been assayed for α-$E_2$.

Cell viability was assessed as described in Example 1a. After the cells had been incubated for 24 or 48 hours in the respective treatment media, cell suspensions were made by decanting media, topically washing each flask with 2 ml 0.02% EDTA, then incubating with 2 ml 0.02% EDTA for 30 minutes. Cells were subsequently resuspended in the appropriate media. 2 ml aliquots of five to six different flasks from each treatment were then treated with 500 μl of 0.4% trypan blue stain (Sigma Chemical Corporation, St. Louis, Mo.). An important limitation of the trypan blue staining method for differentiating dead and live cells is its time dependence. Therefore, care was taken to standardize time between resuspension of the cells, addition of the dye, and actual counting on the hemacytometer.

Figure 8A:
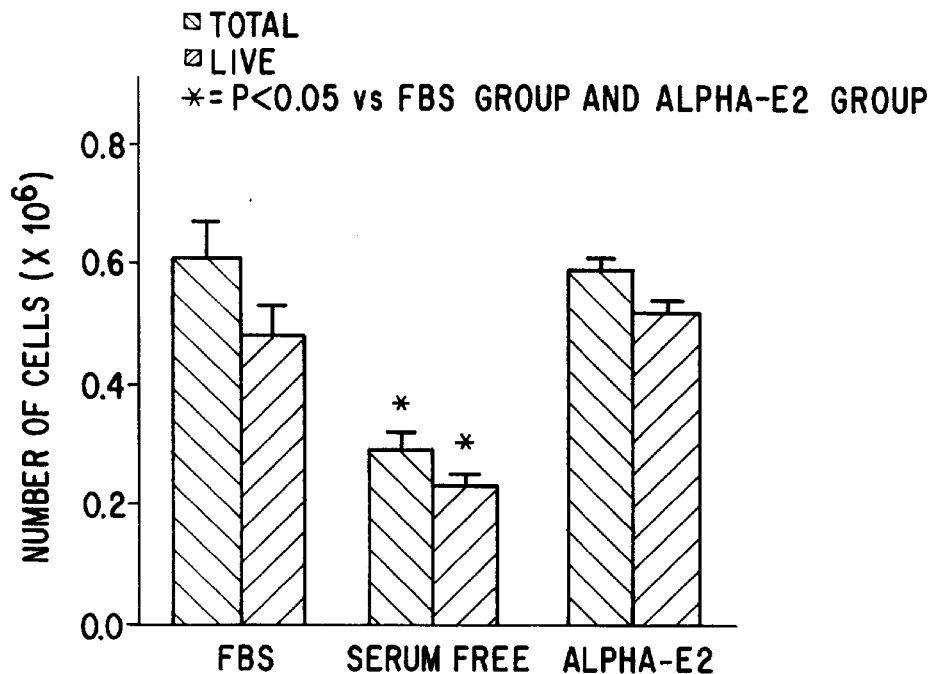
FIG. 8 shows the protective effect of $\alpha$-$E_2$ on SK-N-SH cell viability at 24 hrs. and 8(b) at 48 hrs.
Figure 8B:
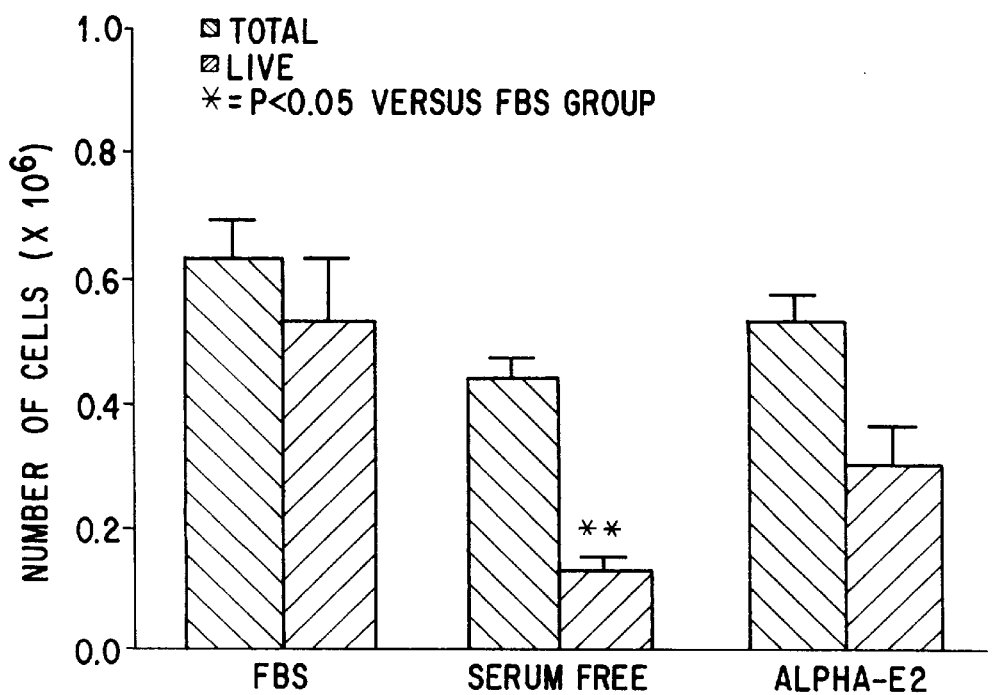

Experimental results. As in Example 1a, the ratio of dead to total cells increased 2–3 fold with the removal of FBS from the culture media (FIG. 8). The addition of α-estrogen prevented this serum removal effect and produced ratios similar to those observed in the FBS group at each sample time.

Example 1c.

Estrogen Delays or Prevents Time-Dependent Death of Cells in Primary Cortical Neuron Cultures.

Experimental design. Primary cortical neurons were produced from rat brains that were 0–1 day old using a variation of methods described by Monyer et al. 1989, *Brain Research* 483:347–354. Dispersed brain tissue was grown in DMEM/10% PDHS (pregnant donor horse serum) for three days and then treated with cytosine arabinoside (ARC) for two days to remove contaminating glial cells. On day 5, the ARC media was removed and replaced with DMEM/10% PDHS. The neuronal cells were cultured for a further 4–7 days before use.

Control primary neuronal cultures show progressive cell death between days 12 and 18 in culture. Twelve cultures were evaluated on days 12 and 16 for levels of the enzyme lactate dehydrogenase (LD) after adding estrogen to 6 cultures maintained in DMEM and 10% PDHS on day 9 and maintaining the remaining cultures as controls. LD was assayed using a variation of the method by Wroblewski et al. 1955, *Proc. Soc. Exp. Biol. Med.* 90:210–213. LD is a cytosolic enzyme which is commonly used in both clinical and basic research to determine tissue viability. An increase in media LD is directly related to cell death.

Figure 1:
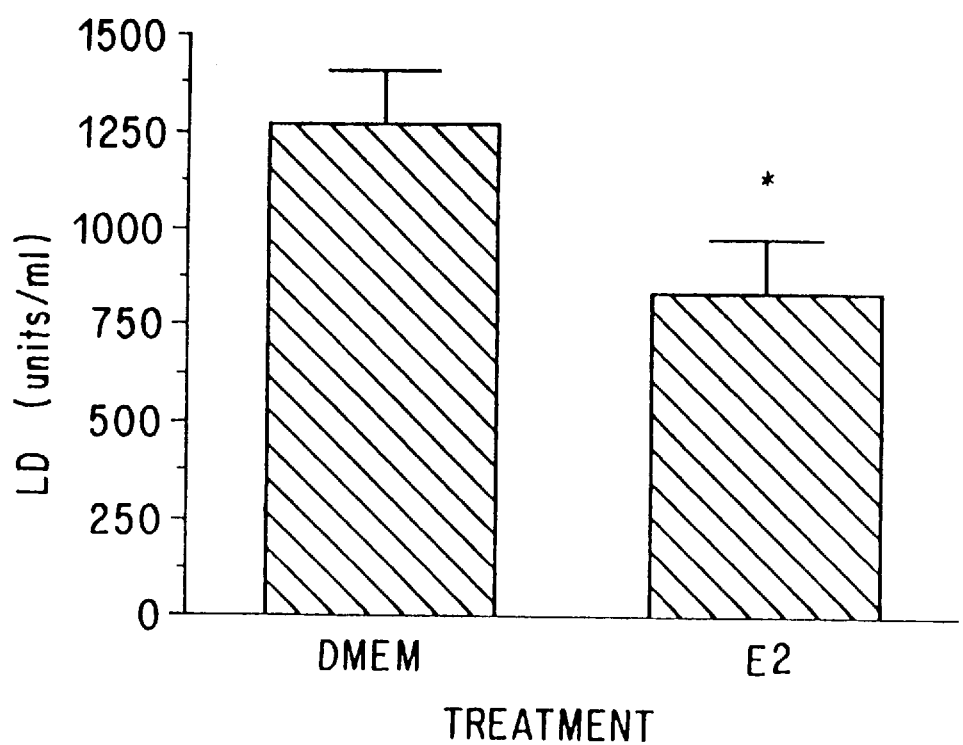
FIG. 1 shows a histogram of the effects of 17β-estradiol ($E_2$) on the age related release of lactate dehydrogenase (LD) in primary cortical neuronal cultures.

Results. A single treatment on day 9 with estrogen significantly reduced ($p < 0.05$) the increase in LD observed in all 6 replicates on days 12 and 16. These data suggest that in primary neurons, estrogen exposure delays or prevents time-dependent death in culture for at least 7 days (FIG. 1), an observation that is further supported by examination of cultures by light microscopy. Here it was observed that estradiol prevented the retrograde degeneration (regression of neuronal extensions) and reduced the appearance of cytosolic inclusions (clusters of material) in cell bodies; both of which are normally observed with aging in primary neuronal cultures in vitro and with degenerative disorders in vivo.

Example 2a.

In Vitro Studies Show that Estrogen Compounds Protect Cells against Cytotoxicity Induced by Hypoglycemia.

Experimental approach. C6 glioma cells obtained from ATCC were plated in RPMI media with FBS at a concentration of $1 \times 10^6$ cells/ml in Falcon® 25 cm$^2$ tissue culture flasks. Four hours prior to the onset of hypoglycemia, the maintenance media was discarded, monolayers were washed twice in the appropriate media and then incubated for four hours at 37° C. in either serum free or serum free plus 544 pg/ml $E_2$. Kreb's Ringer Phosphate buffer was used to wash the monolayers twice before the addition of appropriate glucose treatment. RPMI medium contains 2 mg glucose/ml; flasks were divided into groups of 6 each receiving 100% glucose (2 mg/ml), 80% glucose (1.6 mg/ml), 60% glucose (1.2 mg/ml) or 0% glucose (buffer) with no steroid addition or supplemented with 544 pg/ml $E_2$. All flasks were incubated for 20 hours and then evaluated for total, live, and dead cell number utilizing the trypan blue method previously described.

Figure 2:
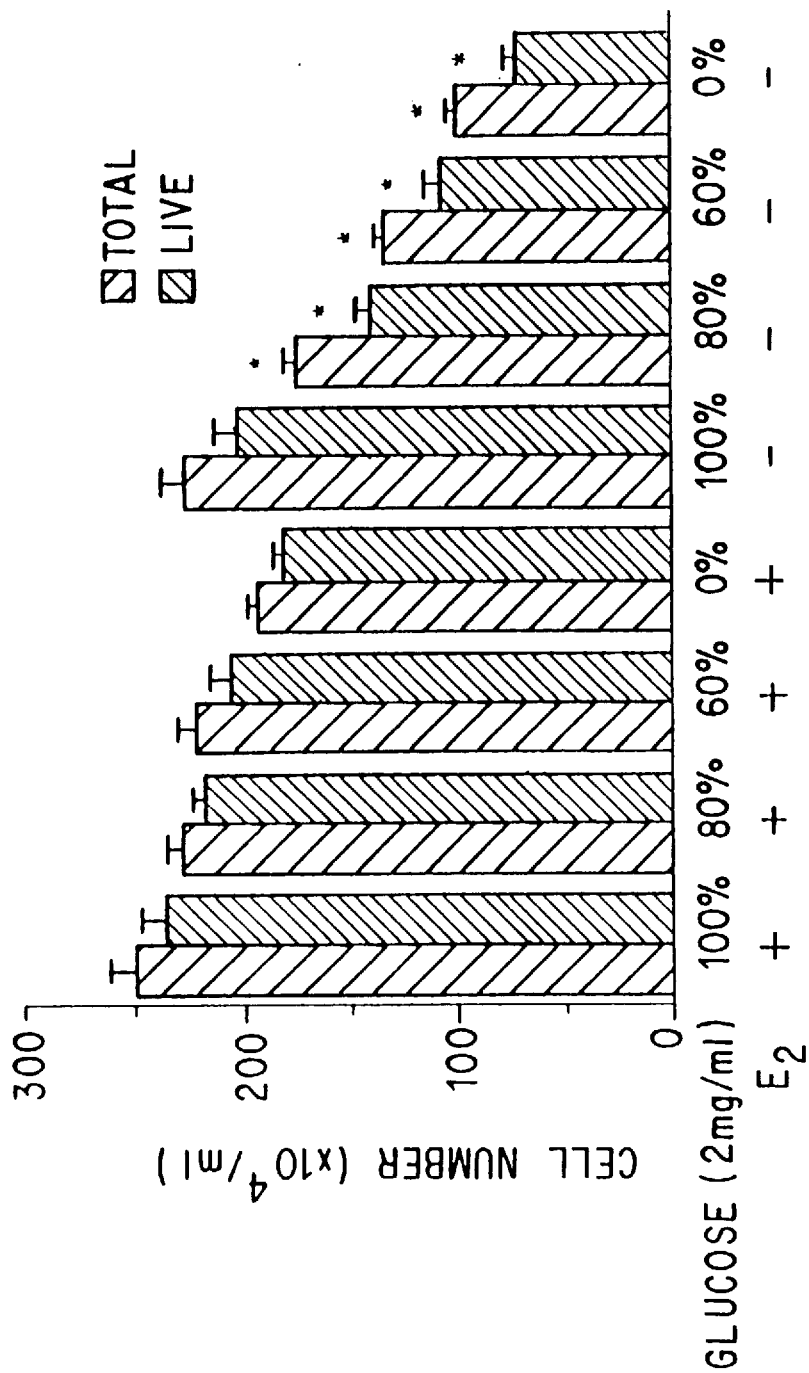
FIG. 2 shows a histogram of the protective effects of $E_2$ on the cytotoxicity induced by various levels of hypoglycemia in C6 cells.

Results. FIG. 2 shows that hypoglycemia caused a marked and dose-dependent reduction in both total and live C6 cell numbers in control flasks, which did not receive $E_2$ treatment. By contrast, at each of the levels of hypoglycemia tested, $E_2$ exposure prevented the loss in total and live cells associated with hypoglycemia. Trypan blue stains dying cells that have become permeable to the dye. In adverse conditions, the number of cells in the total cell population that is measured is diminished as a result of disintegration of dead cells. Hence, the total cell numbers of cells in samples maintained for 20 hours in suboptimal levels of glucose show a reduction in total cell number in FIG. 2. However, a large percentage of this diminishing population are live cells. The addition of estradiol to cultures, maintained in suboptimal levels of glucose, protects the population from cell death and results in an overall greater number of live cells. The asterisk marks those samples having a statistically significant reduction in total cells and live cells in the absence of estrogen when compared to samples in the presence of estrogen.

Example 2b

Estrogen Compounds Protect Cells from Cytotoxicity Induced by Preexisting Hypoglycemia.

Experimental design. C6 cells were cultured as described in Example 2a. On the day of the experiment, flasks (5 to 6 per treatment group) were divided into 5 groups. One group was maintained in normal glucose media (euglycemia: 2 mg/ml glucose in RPMI) and the remaining 4 groups were placed in RPMI with 80% of normal glucose concentration (hypoglycemia). At one hour or at 4 hours after the initiation of the hypoglycemia state, flasks were treated with either RPMI (controls) or with $E_2$ (544 pg/ml RPMI). At 24 hours after the initiation of hypoglycemia, total, live and dead cells were counted as described above. This study design permitted the determination of the time-course of C6 cell rescued from the cytotoxic effects of hypoglycemia.

Results. The results are shown in Table IV and demonstrate the ability of $E_2$ to rescue C6 cells from the cytotoxic effects of a preexisting hypoglycemia state. The number of live cells was increased by more than 2-fold and the number of dead cells was reduced by half after treatment with $E_2$ at one hour after the initiation of hypoglycemia. In contrast, treatment with $E_2$ at 4 hours after the initiation of hypoglycemia had no effect on live cell number and only slightly reduced dead cell number.

TABLE IV

Demonstration of the Ability of $E_2$ to Rescue C6 Cells from the Cytotoxic Effects of Hypoglycemia.

| Glucose Pretreatment | N | Treatment | Time | C6 Cell Number ($^\# \times 10^4$/ml) Total | Live | Dead |
|---|---|---|---|---|---|---|
| Euglycemia | 6 | — | — | 243 ± 16 | 235 ± 16 | 9 ± 2 |
| Hypoglycemia | 6 | SF − $E_2$ | 1 hr. | 108 ± 7 | 19 ± 3 | 89 ± 6 |
|  | 5 | SF + $E_2$ | 1 hr. | 92 ± 7 | 44 ± 5* | 49 ± 4* |
|  | 6 | SF − $E_2$ | 4 hr. | 124 ± 10 | 17 ± 2 | 107 ± 8 |
|  | 6 | SF + $E_2$ | 4 hr. | 93 ± 9 | 19 ± 4 | 74 ± 7 |

Depicted are mean ± SEM.
SF = Serum Free RPMI media.
*P < 0.05 from Serum Free group at 1 hour.

Example 2c

Estrogen Compounds can Protect Cells against Cytotoxicity Induced by Excitotoxic Amino Acids.

Experimental design. Five culture dishes containing SK-N-SH neuroblastoma cells were treated with $E_2$ (544 pg/ml) and 5 culture dishes were treated with RPMI media as described above. Four hours later, all cell were treated with NMDA (500 μM) for 5 minutes. Total live cells and dead cells were then determined.

Figure 3:
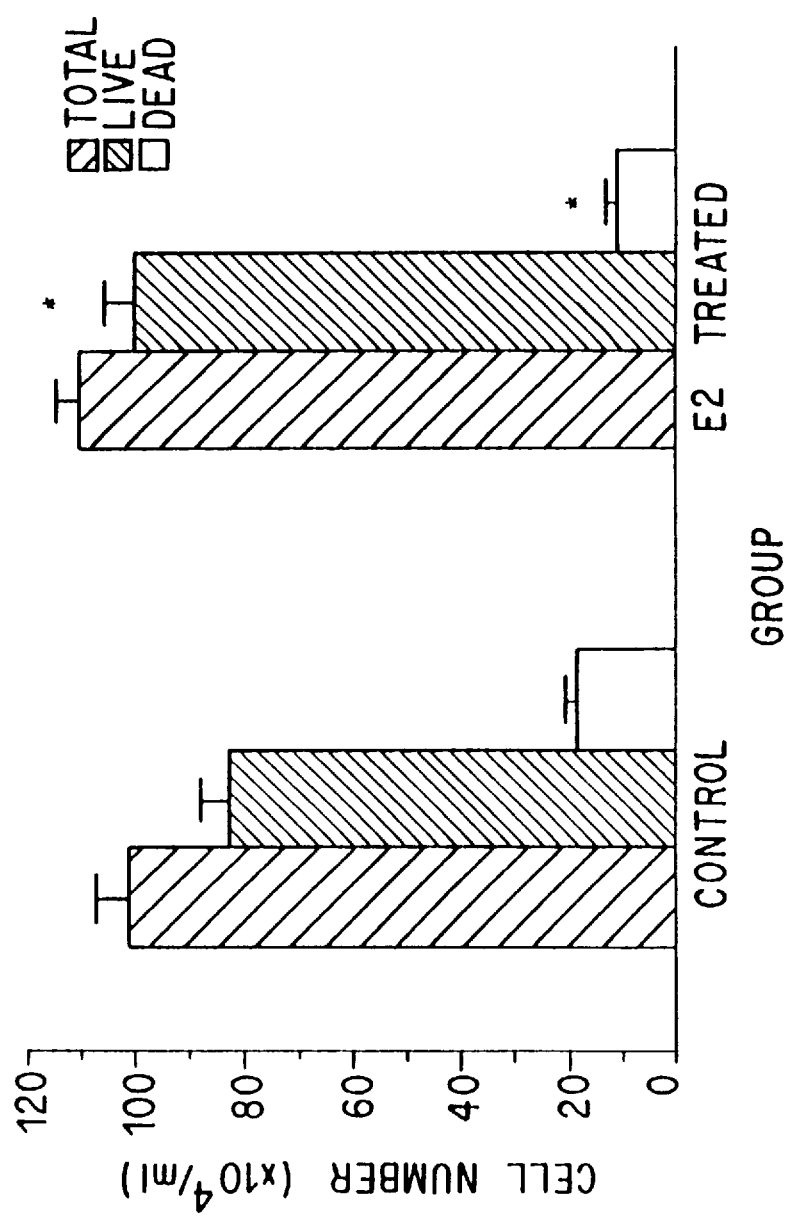
FIG. 3 shows a histogram of the protective effects of $E_2$ on the cytotoxic effects of N-methyl D-aspartate (NMDA) in neuroblastoma cells.

Results. The protective effect of estradiol on the viability of the cell population is shown in FIG. 3. Pretreatment with estradiol increased the number of live cells and reduced the number of dead cells in these neuroblastoma cultures following treatment with NMDA. These data demonstrate that $E_2$ pretreatment protects cells from the neurotoxicity associated with excitotoxic amino acids.

Example 3

In Vivo Studies Show Behavioral Improvements caused by the Neuroprotective effect of Estrogen Compounds.

The role of estradiol in protecting cholinergic function in the CNS and the association of this effect with learning and memory has been demonstrated as described below.

Example 3a

Learning and Memory Improve in Estrogen Treated Ovariectomized Rats.

Experimental design. Three groups of animals were analyzed using a standard 2-way active avoidance paradigm. The three groups of animals were: ovary-intact, ovariectomized, and estradiol-replaced ovariectomized animals.

Animals. Young adult female (3–4 months old) CD-Sprague-Dawley rats (Charles River Breeding Laboratories, Wilmington, Mass.) were maintained in standard breeding conditions.

Animal surgical procedure: Animals were anesthetized with methoxyflurane (Metofane, Pitman-Moore, Washington Crossing, N.J.). Two-thirds of the rats underwent bilateral ovariectomy using a dorsal approach. Three weeks following ovariectomy, a subset of the ovariectomized animals (the $E_2$ replaced group) received a 5 mm Silastic® (Dow Corning, Midland, Mich.) pellet containing a 1:1 mixture of cholesterol (Steraloids, Inc., Wilton, N.H.) and 17-B estradiol that was implanted subcutaneously. Estradiol delivery through Silastic® tubing results from diffusion down a large concentration gradient and the fibrosis, which occurs over time around the Silastic® pellet, reduces diffusion. The $E_2$ replacement regimen was maintained for 2 or 25 weeks following the 3 week rest period after ovariectomy. At 5 weeks and 28 weeks post ovariectomy, animals were behaviorally tested. In the long term treatment regimen, we removed and repositioned the Silastic® pellets every 2 to 3 weeks to maintain $E_2$ diffusion from the Silastic. The ovariectomized group received sham pellets that were similarly re-positioned every 2 to 3 weeks. Both $E_2$ and sham pellets were washed twice with 100% ethanol and were then incubated in PBS at room temperature for 48 hours prior to implantation. The resulting experimental groups were: ovary intact (INTACT), ovariectomized (OVX) (5 or 28 weeks), and estradiol-replaced ($E_2$ pellet).

Behavioral testing; active avoidance. To assess learning, the 2-way active avoidance paradigm was employed following the procedures of Mouton et al. 1988, Brain Research 444:104–108. All three groups of animals were tested for 14 consecutive days, each day consisting of 15 trials. Each trial lasted for 1 minute; and consisted of the simultaneous presentation of conditional stimuli (a light and sound cue) for the first 5 seconds and a 7 second interval followed by an electrical foot-shock of 1.4 mA for a 2 second duration. Successful learning was determined by the number of correct responses or "avoidances" and was defined as transferring from one side of the shuttle-box to the other within the first 12 seconds of each trial, before the onset of the footshock. In order to assess potential motivational differences between animals in different treatment groups, the number of "no transfers" were also recorded. This parameter describes the number of trials in which the animal did not transfer from one side of the shuttle box to the other upon stimulation with the electrical shock.

Statistical analyses. Behavioral data were analyzed non-parametrically using the Kruskal-Wallis one-way analysis of variance and the Mann Whitney U test for assessment of group differences.

Figure 4:
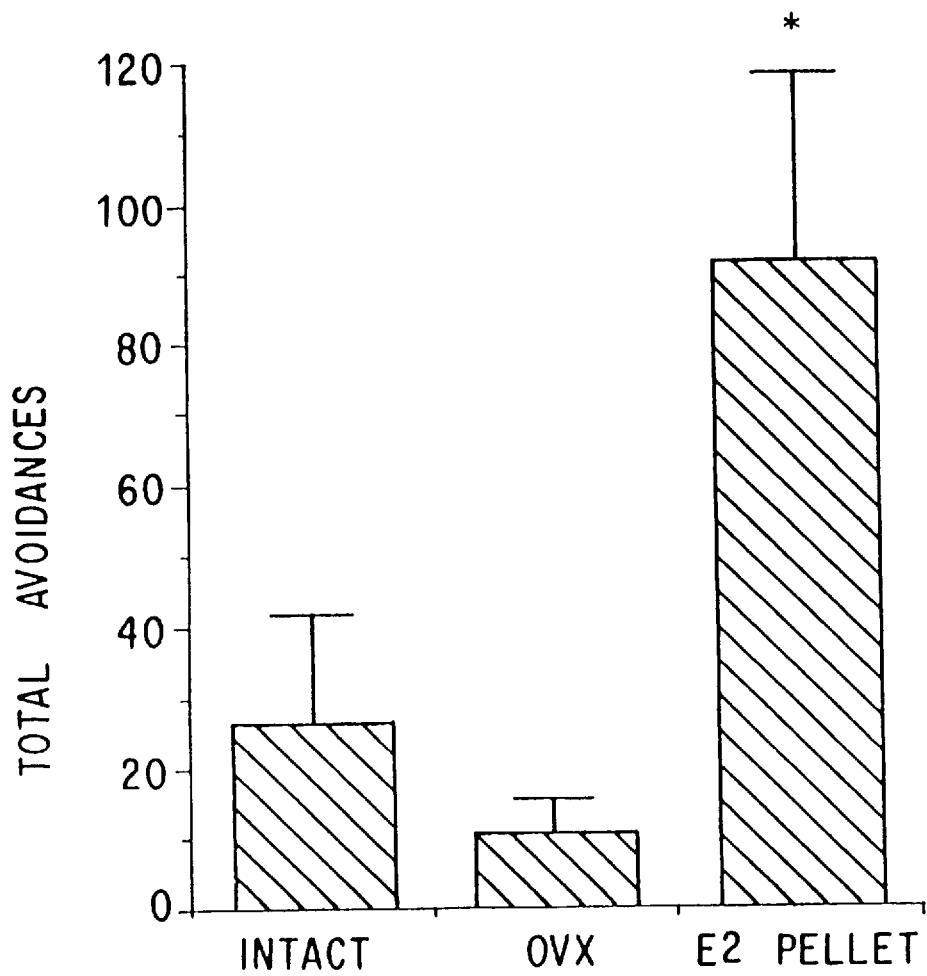
FIG. 4 shows active avoidance performance following 5 weeks of ovariectomy in intact, ovariectomized and $E_2$ replaced animals.
Figure 5:
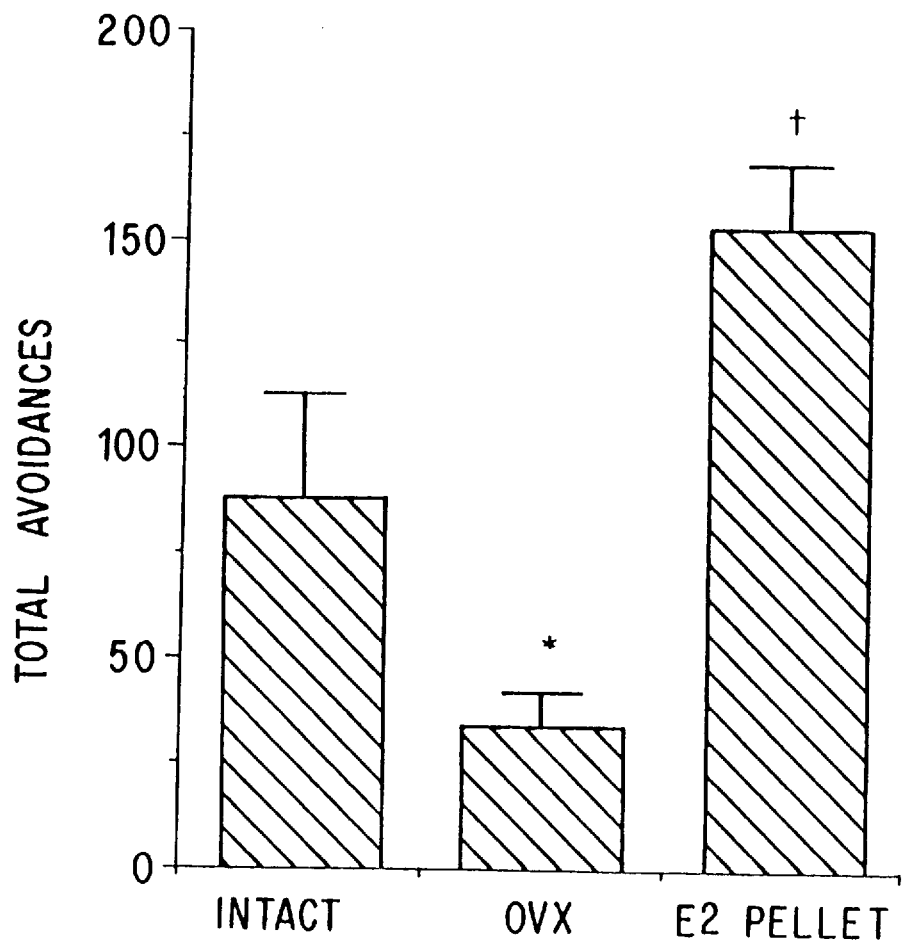
FIG. 5 shows active avoidance performance following 28 weeks of ovariectomy in intact, ovariectomized and $E_2$ replaced animals.

Results. INTACT and $E_2$-pellet animals performed better on the 2-way active avoidance paradigm relative to OVX animals. FIGS. 4 and 5 show the average of the total number of avoidances made by each animal over the 14 day testing period starting at the end of the 5 week and 28 week period in the three groups of animals. OVX rats showed a 59% decrease in the number of avoidances achieved relative to the intact group, but this difference was not significant. $E_2$ replacement of OVX rats caused a 8.5-fold increase in the number of avoidances relative to the OVX group. When these same animals were maintained on their respective treatments and were behaviorally tested at 28 weeks, the number of total avoidances was increased in all groups relative to the 5 week testing period (FIGS. 4 and 5.) However, at this 28 week testing point, OVX significantly reduced the total number of avoidances by 61% and $E_2$ replacement continued to increase avoidances by 4.5-fold versus OVX rats. Furthermore, $E_2$-pellet rats showed a marked acceleration in their rate of learning at 28 weeks, achieving the criteria of performing correctly 11 out of a possible 15 times in a given day by 1.3±0.3 days of testing (Table V). INTACT rats did not show this acceleration in learning requiring 9±2.8 days to reach criteria. The OVX animals maintained their inability to learn the task in the allotted 14 days and were therefore assigned a value of 15 days.

At both 5 and 28 weeks, rats in each group maintained their relative order of proficiency in active avoidance and all animals performed better in the second trial than first (FIGS. 4 and 5). This enhanced performance during the second exposure to the paradigm likely reflects recall of the behavior learned during the first test. This long-term memory is particularly apparent in the $E_2$-pellet group, which at the 28 week time-point, reached the performance criteria in 1.3±0.3 days (Table V). It appears that chronic exposure to low doses of $E_2$ may enhance long-term memory in addition to its stimulation of learning of this active avoidance paradigm.

TABLE V

Effect of Short-Term and Long-Term Ovariectomy and Estradiol Replacement on Learning and Retention

| Treatment Group | Days to Reach Criteria | |
|---|---|---|
| | 5 weeks (acute) | 28 weeks (chronic) |
| INTACT | 14.0 ± 9.0 | 9.0 ± 2.8 |
| OVARIECTOMIZED | 15.0 ± 0.0 | 15.0 ± 0.0 |
| $E_2$ PELLET | 9.5 ± 2.1# | 1.3 ± 0.3* | p ≤ 0.05 vs Ovariectomized and Intact animals.
*p ≤ 0.05 vs Ovariectomized animals using the Mann-Whitney U nonparametric statistic.

Example 3b

Neurochemical Assays Demonstrate the Neuroprotective Effect of Estrogen.

Biochemical tests were performed on enzymes normally produced by healthy cholinergic neurons to establish whether a cytoprotective effect could be detected in vivo and correlated with behavioral improvements.

Experimental design. Two assays were used to measure the viability of neurons. These assays were high affinity choline uptake (HACU) and choline acetyl transferase (ChAT) activity. HACU was conducted on tissues from both the frontal cortex and hippocampus of the rats. The effect of different lengths of time following ovariectomy or $E_2$ replacement on behavior (active avoidance behavior) and on the activity of cholinergic neurons (HACU and choline acetyl transferase (ChAT) activity) as measured.

Female Sprague-Dawley rats were either ovariectomized (OVX) only, or ovariectomized for 3 weeks followed by subcutaneous implantation of a silastic pellet containing 17-β-estradiol ($E_2$ pellet) resulting in a replacement of $E_2$ to physiological levels. Ovary intact animals served as a positive control. Active avoidance behavior and choline acetyltransferase (ChAT) activity in the frontal cortex and hippocampus were assessed at 5 weeks and 28 weeks post ovariectomy while high affinity choline uptake (HACU) was measured only at the 5 week time point.

Active Avoidance Test. This test was carried out as described in Example 3a.

Biochemical Analyses.

(a) Plasma estradiol assay. Following behavioral testing, or in the case of the untested animals following the period of treatment, animals were decapitated and trunk blood was obtained. The blood was centrifuged at 13,500×g for 1.5 minutes and resulting plasma was aliquoted into a separate tube for estradiol level determination at a later date. Plasma concentrations of $E_2$ were assayed by radioimmunoassay (RIA) using commercial kits supplied by Diagnostic Product Corp. (Los Angeles, Calif.). The range of assay detectability was 20–3600 pg/ml. All samples were quantified in a single assay.

(b) High Affinity Choline Uptake (HACU). HACU was assessed in behaviorally naive animals. Following decapitation, brains were removed from the skull and placed on an ice-cooled surface. The hippocampus and frontal cortex were then dissected and immediately placed into ice cold 0.32M sucrose buffer (0.32M sucrose, 1.0 mM EDTA, 100 μM TRIS-HCl, pH=7.4 at 4° C.). Average wet weights for the tissue regions dissected were 0 mg and 110 mg for the frontal cortex and hippocampus, respectively. Tissue samples were then homogenized with a dounce homogenizer at 400 rpm. Homogenized samples were subsequently centrifuged at 1000×g for 8 minutes at 4° C. The supernatant (S1 fraction) was centrifuged at 30,000×g for 15 minutes at 4° C. Following this spin, the supernatant was discarded and the resulting pellet (P2 fraction) was resuspended in 2 ml of cold, oxygenated Krebs buffer (139 mM NaCl, 5 mM KCl, 13 mM $NaHCO_3$, 1 mM $MgCl_2$, 1 mM $NaH_2PO_4$, 10 mM glucose, 1 mM $CaCl_2$; and was oxygenated for 15 minutes with 95% $O_2$/5% $CO_2$). High affinity choline uptake was determined in triplicate in the presence of 1 μM [3H]-choline (final specific activity: 4.5 Ci/mmol, New England Nuclear, Cambridge, Mass.). Non-specific uptake was estimated by adding 5 μM hemicholinium-3 (Sigma Chemical Corp., St. Louis, Mo.); these hemicholinium-3 values were subtracted from total counts to obtain high affinity values. Each reaction tube contained 200 μl of P2 suspension. Unused tissue was stored at −30° C. for subsequent determination of ChAT activity and protein levels. Analysis of protein in the P2 preparation was conducted according to the method of Bradford using Coomassie Blue Dye (5).

HACU differences were analyzed using a t-test since INTACT versus OVX and OVX versus $E_2$-treated were evaluated only once each in two separate studies. Analysis of variance (ANOVA) was employed for other neurochemical analyses. Multiple comparisons among groups were performed using Scheffe's post-hoc test.

(c) ChAT assay. ChAT activity was determined in both behaviorally naive animals (5 week group) as well as the behaviorally tested group (28 week group). ChAT was assayed following a modified version of Fonnum 1975, J. Neurochem. 24:407–409. P2 samples were thawed and sonicated in the presence of 1% l-butanol and centrifuged at 13000×g for 5 min. 20 μl of the resulting supernatant was used in each reaction tube. The reaction mixture contained 0.28 mM [3H]-ACoA (specific activity: 45 μCi/mol, New England Nuclear, Cambridge, Mass.), 7.8 mM choline chloride and 0.2 mM physostigmine (Sigma Chemical Corp., St. Louis, Mo.). Incubation with the [3H]-ACoA was carried out for 30 min. The reaction was terminated by the addition of ice cold glycyl-glycine buffer (GLY-GLY) at pH 8.6. Following a 10 minute incubation at 4° C., tetraphenyl boron dissolved in butyronitrile (10 mg/ml) was added to the reaction tube allowing for liquid cation exchange extraction of acetylcholine (ACh). Samples were vortexed and centrifuged in a bucket centrifuge at low speed (185×g) for 5 minutes to allow settling and separation of the organic and aqueous phases. 100 μl of the organic phase was then aliquoted into 7 ml scintillation vials and 4 ml of scintillation fluid (Liquiscint®, National Diagnostics, Atlanta, Ga.) were added. Vials were then counted in a Hewlett-Packard scintillation counter for 5 minutes each, the dpm were converted to pmoles and values were normalized for protein content.

Results.

(a) Estradiol concentrations. Serum $E_2$ concentrations ere 43±10 and 36±5 pg/ml for the INTACT and $E_2$-pellet groups, respectively. Ovariectomy reduced serum $E_2$ concentrations to below the sensitivity of the radioimmunoassay employed (20 pg/ml) in all but 5 animals sampled. These 5 animals, however, had serum levels that were very close to the sensitivity limit of the assay.

Figure 6:
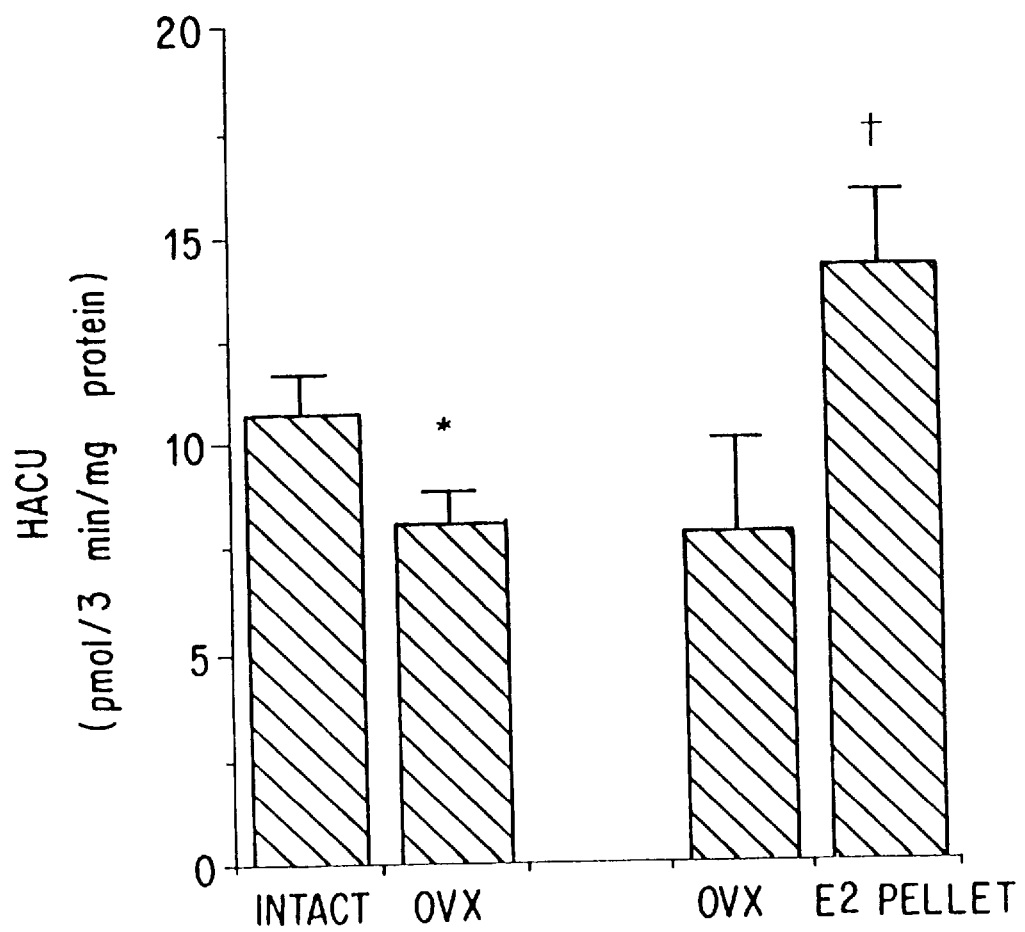
FIG. 6 shows the effect of 5 week ovariectomy and $E_2$ replacement on high affinity choline uptake in the frontal cortex of behaviorally naive rats.
Figure 7:
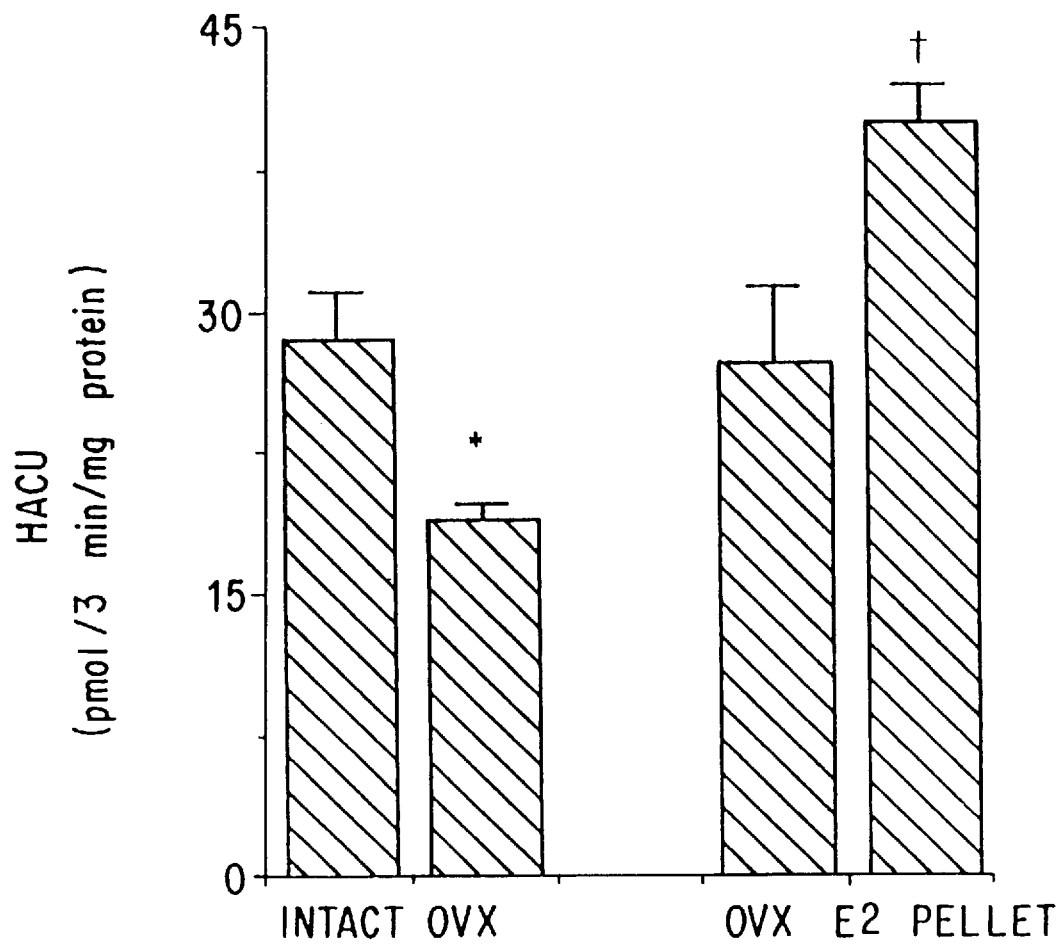
FIG. 7 shows the effect of 5 week ovariectomy and $E_2$ replacement on high affinity choline uptake in the hippocampus of behaviorally naive rats.

(b) High Affinity Choline Uptake. Ovariectomy significantly reduced HACU by 24% in the frontal cortex (FIG. 6) and by 34% in the hippocampus (FIG. 7). $E_2$-replacement resulted in a reversal of this effect of ovariectomy, increasing HACU by 82% in the frontal cortex (FIG. 6) and by 46% in the hippocampus (FIG. 7). Because HACU is a measure of cholinergic activity, it is concluded from these results that estradiol reverses the decline of cholinergic activity in the frontal cortex and hippocampus and further stimulates activity of cholinergic projections to these regions.

(c) Choline Acetyl Transferase activity. In the frontal cortex, no significant differences in ChAT activity were detected within 5 weeks of ovariectomy (Table VI). At the 28 week time point, CHAT levels in the frontal cortex were reduced in both the INTACT and OVX groups by 61% and 56%, respectively. In the $E_2$-pellet group, however, this reduction was only 16%. In the hippocampus, five weeks of ovariectomy was a sufficient time period to induce a significant reduction in CHAT activity, and 3 weeks of $E_2$-replacement reversed this effect (Table VII). The reductions in hippocampal ChAT activities in INTACT and OVX animals between 5 and 28 weeks were comparable with those seen in the frontal cortex. In $E_2$-pellet animals, loss of hippocampal ChAT activity was larger than that seen in the frontal cortex but was less than that seen in OVX or INTACT animals.

TABLE VI

Effect of Short Term and Long Term Ovariectomy and Estradiol Replacement on Choline Acetyltransferase Activity in the Frontal Cortex

| Treatment Group | ChAT activity (nmol/30 min/mg protein) | |
|---|---|---|
| | 5 weeks | 26 weeks |
| INTACT | 10.2 + 0.5 | 4.0 + 0.1 |
| OVARIECTOMIZED | 9.2 + 0.6 | 4.0 + 0.2 |
| $E_2$ PELLET | 9.8 + 0.6 | 8.2 + 0.8* | n = 6 for ovariectomized and $E_2$ pellet groups for the 5 week time period.
n = 5 S for intact group for the 5 week time period.
n = 6 for all treatment groups for the 28 week time period.
p ≦ 0.05 vs intact group and OVX group.

TABLE VII

Effect of Short Term and Long Term Ovariectomy and Estradiol Replacement on Choline Acetyltransferase Activity in the Hippocampus.

| Treatment Group | ChAT activity (nmol/30 min/mg protein) | |
|---|---|---|
| | 5 weeks | 28 weeks |
| INTACT | 13.2 + 0.8 | 5.7 + 0.3 |
| OVARIECTOMTZED | 10.3 ± 0.3* | 6.2 ± 1.1 |
| $E_2$ PELLET | 12.7 ± 0.5 | 8.0 ± 1.1 | n = 6 for ovariectomized and $E_2$ pellet groups for the 5 week time period.
n = 5 for intact group for the 5 week time period.
n = 6 for all treatment groups for the 28 week time period.
*p ≦ 0.05 vs. intact group and $E_2$ pellet group.

Example 4a

In Situ Hybridization Demonstrates Increased Levels of Brain Derived Neurotrophic Factor (BDNF) mRNA is Stimulated by Estradiol.

This example demonstrates that estrogen can stimulate the production of neurotrophic growth factors such as BDNF.

Experimental design. Animals were ovariectomized for 12 weeks, while $E_2$ treated animals were ovariectomized for 3 weeks followed by 9 weeks of $E_2$ treatment. A second set of animals were ovariectomized for 28 weeks and the $E_2$ treated animals were similarly ovariectomized for 3 weeks followed by 25 weeks of $E_2$ replacement. Intact control animals were run in parallel with each set of animals. The rats were deeply sedated with sodium pentobarbital. Immediately following, the brains of these animals were transcardially perfused with 4% paraformaldehyde in 0.1M phosphate buffer. On the following day, the brains were removed from the skull and immersed in a series of solutions (cold 4% paraformaldehyde solution for 2 days at 4° C. followed by a 4% paraformaldehyde solution containing 20% (wt/vol) sucrose). After removal from the sucrose solution, the brains were blocked (removed olfactory bulbs, brainstem and cerebellum), frozen on dry ice and immediately stored at −80° C. until time of use. 25 μm slices of the brain were made using a microtome and placed in a 4% paraformaldehyde solution. Within 3 weeks, the slices were hybridized according to the method described by Gall et al. 1989, *Science* 245:758–761. The BDNF probe was 750 b.p. of rat BDNF cDNA, corresponding to the entire amino acid coding region. The probes were labeled with $^{35}S$ using the T3 polymerase kit. The hybridized slices were mounted onto Vectabond treated slides and exposed to autoradiographic film for 4 days. The varying intensities of radioactive signal on each slice (the hybridization signal) was translated into differing optical densities on film and was analyzed using the BRS 2 Imaging System (Imaging Research Inc.). The relative optical densities and the background levels were recorded. Signal was defined as the optical density of the region divided by the average background level as assessed by parts of the film adjacent to the brain slice. In the imaging system employed, the higher the O.D., the lower the signal. As such, the data were transformed to the inverse of the signal to noise ratio in order to facilitate the presentation of the data.

Results. Ovariectomy resulted in a significant reduction in the BDNF signal in cortical sections relative to INTACT controls. Estradiol replacement of ovariectomized rats increased the BDNF signal to that normally observed in INTACT controls. The data in Table VIII derived multiple slices of the cerebral cortex of an animal in each treatment group demonstrate the stimulatory effect of an estrogen on BDNF synthesis.

TABLE VIII

Relative Level of BDNF mRNA in the Cortex of Intact, Ovariectomized and $E_2$ Pellet Animals

| Treatment Group | BDNF Level |
|---|---|
| INTACT | 1.242 ± 0.035 |
| OVARIECTOMIZED | 1.159 ± 0.023* |
| $E_2$ PELLET | 1.224 ± 0.026 |

*p ≦ 0.05 vs Intact and $E_2$ Pellet animals.

Example 4b:

In Vivo Studies Demonstrate Increased Levels of NGF mRNA Stimulated by Estradiol.

This example demonstrates that estrogen can stimulate the production of neurotrophic growth factors such as NGF. Similarly treated animals as in example 4a were used to measure levels of NGF mRNA using the dot blot technique.

Animals were ovariectomized for 12 weeks, while $E_2$ treated animals were ovariectomized for 3 weeks followed by 9 weeks of $E_2$ treatment. RNA was isolated from the frontal cortex and hippocampus using acid guanidinium isothiocyanate followed by phenol/chloroform extraction. The use of the dot blot technique was first validated by performing Northern blots to ensure that hybridization with our NGF probe of 771 b.p. recognizing the entire pre-pro sequence of NGF, resulting in a single band corresponding to the length of NGF mRNA. The NGF mRNA signal was normalized to the amount of RNA loaded as estimated by the amount of signal produced by subsequent actin hybridization.

Following 3 months of ovariectomy, NGF mRNA levels were significantly reduced (45%) in the frontal cortex (Table IX). $E_2$ treatment resulted in a partial recovery, albeit non-statistically significant from the OVX group. Hippocampal NGF mRNA was not found to differ from controls using this method of detection. $E_2$ treatment did, however, result in a significant increase in NGF mRNA levels (Table IX).

TABLE IX

The Effect of Three-Month Ovariectomy and Estrogen Replacement on NGF mRNA Levels in the Frontal Cortex and Hippocampus

| Treatment | NGF mRNA (units per μg actin) | |
| --- | --- | --- |
| | Frontal Cortex | Hippocampus |
| INTACT | 0.622 ± 0.067 (n = 10) | 0.590 ± 0.052 (n = 6) |
| OVARIECTOMIZED | 0.342 ± 0.050# (n = 12) | 0.616 ± 0.051 (n = 12) |
| $E_2$ REPLACED | 0.453 ± 0.070 (n = 8) | 0.803 ± 0.082* (n = 12) | p ≤ 0.05 vs Intact.
*p ≤ 0.05 vs Ovariectomized.

Example 5

Proposed Evaluation for the in Vivo Effects of Estrogens in Excitatory Amino Acid Neurotoxicity.

Adult female rats are ovariectomized and two weeks later are treated with a "Silastic" pellet containing cholesterol (controls) or estradiol in amounts sufficient to elevate plasma estradiol levels in the physiologic range. After 1 to 2 weeks of such estrogen-replacement therapy, rats receive an intracerebral injection of N-methyl-D-aspartate (NMDA) or artificial cerebrospinal fluid in amounts to induce extensive toxicity of brain neurons.

As an endpoint of the study, the number of neurons in the hippocampal CAI region and the number of neurons in the cerebral cortex are determined. In addition, nerve terminals in both regions would be stained for detection choline acetyltransferase, the marker enzyme for cholinergic neurons.

It is expected that estrogen-replacement therapy will reduce or eliminate the loss of nerve cells in both the hippocampus and in the cerebral cortex. Such a result teaches that physiological estrogen-replacement can protect brain cells from the neurotoxic effects of excitatory amino acids.

Example 6

Estrogen Enhances Cerebral Glucose Uptake at Sites in the Brain.

The effect of estradiol benzoate ($E_2B$) on cerebral glucose uptake in various brain regions which contain variable numbers of $E_2B$ receptors is described and the determination concerning increases in the amount of glucose transported into the brain in the presence of $E_2B$ is also described for a selected animal model.

Female rats were bilaterally ovariectomized to eliminate endogenous estrogens and two to three weeks later were implanted with an atrial cannula for the i.v. administration of $C^{14}$-2-deoxyglucose ($C^{14}$-2-DG) to unanesthetized rats. Animals were allowed four to five days to recover from the cannulation before the study was initiated.

On the day of the experiment, animals were randomized and assigned to groups which received either $E_2B$ in oil or oil alone (controls) administered subcutaneously at the dose and times described below. In our initial study, animals were treated with oil or $E_2B$ (10 μg/kg body weight) and were sacrificed at 2, 4, 8, 12 or 24 h. In an additional study, rats were treated with oil or $E_2B$ at doses of 1, 10 or 100 μg/kg body weight and were sacrificed 4 h later. Forty-five minutes prior to sacrifice, all rats received a single injection via the atrial cannulae of $C^{14}$-2-DG (25 μCi/ml saline/kg body weight; specific activity 49–53 mCi/mmol, New England Nuclear, Boston, Mass.).

To assess the effects of $E_2B$ on transport of glucose across the blood-brain barrier we used the technique of Oldendorf (Oldendorf, Brain Res. 24:37–46; 1970; and Am. J. Physiol. 221:1629–1638 (1971)). One μCi/ml of $C^{14}$-2-DG (specific activity 49–53 mCi/mmol, New England Nuclear, Boston, Mass.) and approximately five μCi/mi of $^3H_2O$ (specific activity 1 mCi/ml, New England Nuclear, Boston, Mass.) were mixed with Krebs' Ringer Phosphate solution buffered to pH 7.4 with 10 mM HEPES and injected into the carotid artery of female rats.

Fifteen seconds after injection, the animals were killed by decapitation, trunk blood was collected for later assay of serum $E_2B$ concentrations and the brain was removed from the cranium for dissection of the following regions: medial basal hypothalamus (MBH), preoptic area (POA), cortex, hippocampus, striatum, cerebellum and brainstem. The anterior pituitary (AP) was also isolated from the cranium. The dissection of brain tissues followed the methods of Glowinski and Iversen (Glowinski et al., J. Neurochem. 13:655–669 (1966)). Tissues were immediately weighed and placed in scintillation vials for processing. The mg weights (mean ±SEM) of tissues used in these studies were: MBH= 13.4±1.3; POA=10.5±0.5; cortex=38.7±3; hippocampus= 27.7±1.7; striatum=24.3±2; cerebellum=32.5±1.9; brainstem=32.9±1.9 and AP=8.6±0.6.

During the procedure, peripheral plasma glucose values were in the normal range of 90–120 mg %.

Alternatively, half of the brain was dissected rostral to the midbrain and ipsilateral to the injection side, tissue passed through a 20 gauge needle and the sample subjected to routine digestion and then prepared for liquid scintillation counting as described above. An aliquot of original isotope mixture was obtained by recovering the residual mixture in the injection syringes. Both aliquot and tissue samples were then counted for $H^3$ and $C^{14}$ by routine liquid scintillation counting. Uptake by the Brain Uptake Index (BUI) was calculated after correcting for counting efficiency using the following equation for extraction (E):

$$E = \frac{C^{14} \text{ in brain tissue}/^3H \text{ in brain tissue}}{C^{14} \text{ in mixture}/3H \text{ in mixture}} \times 100$$

Table XI provides a sample of data generated within one experiment. Evaluations of the time or dose effect of $E_2B$ on glucose uptake were done using a one way ANOVA. Post hoc comparisons were done with Dunnett's tests. These statistical analyses were performed on raw data (dpms $C^{14}$/mg tissue) by comparing the dpms for the $E_2B$-treated group with its control (oil) group at each dose and at each time point evaluated. For clarity of presentation, the raw data were then expressed as percent of mean control. The magnitude of the response of each $E_2B$-treated animal was determined by calculating the percentage increase of 2-DG uptake relative to the mean value of 2-DG uptake in the oil-treated control group. BUI data were analyzed by a one-tailed t-test for independent samples.

Statistical difference was set at p <0.05 for all tests.

The time course of the effects of a 10 μg/kg body weight dose of $E_2B$ on glucose uptake is shown in Table X. Overall, $E_2B$ increased glucose uptake significantly in ovariectomized rats by 20 to 120% in 7 of 8 regions examined. However, the time at which a significant increase was observed varied among regions. For 5 of 8 regions, the POA, hippocampus, striatum, cerebellum and AP, the peak $E_2B$ effect was observed at 2 to 4 hours, while 2 regions showed peak effects at 12 hours (the MBH and cerebral cortex). Five regions showed a significant decline in glucose uptake at some time-point after an $E_2B$-induced increase. These regions were the POA, the hippocampus, the striatum, the cerebellum and the AP. No significant effect of $E_2B$ on brainstem glucose uptake was observed.

The dose-dependency of the $E_2B$ effect on brain glucose uptake at 4 hours post-$E_2B$ injection is shown in Table XI. The 1 μg/kg dose of $E_2B$ had no effect on brain glucose uptake. In contrast, the 10 μg/kg dose of $E_2B$ increased glucose uptake in 6 of 8 regions examined at the 4 h time point. Furthermore, only two regions exhibited increased glucose uptake at the 100 μg/kg dose of $E_2B$, the MBH and the POA. All other regions examined exhibited a reduced glucose uptake, with three regions, the striatum, the cerebellum and the brainstem, showing a significant reduction.

Serum $E_2$ concentrations were observed to increase in a dose-dependent manner 4 h post $E_2B$ injection. The 1 μg/kg $E_2B$ dose did not elevate serum $E_2B$, levels above those observed in ovariectomized rats, the 10 μg/kg $E_2B$ dose increased serum $E_2B$, levels into the physiological range, and the 100 μg/kg dose increased serum $E_2B$ levels, which were 12 to 30 times those seen during peak serum $E_2B$ concentrations on proestrus. Peak serum $E_2B$ levels were observed at 4 hours after administration of a 10 μg/kg dose of $E_2B$.

Our evaluation of BUI using the Oldendorf method indicates that 4 h of exposure to $E_2B$ increased the transport of glucose across the blood-brain barrier by about 40%. The 40% increase in BUI was accomplished by an $E_2B$-induced increase in $C^{14}$-2-DG extraction with no change in $^3H_2O$ extraction across the blood-brain barrier (Table XII).

It is expected that estrogen-replacement therapy will reduce or eliminate the loss of nerve cells in both the hippocampus and in the cerebral cortex. Such a result would indicate that physiological estrogen-replacement can protect brain cells from the neurotoxic effects of hypoglycemia.

Although certain preferred embodiments of the present invention have been described, the spirit and scope of the invention is by no means restricted to what is described above. For example, while the examples describe experiments performed in rats and cultured cells, it is believed that these are accurate models for predicting activity of compounds in humans.

TABLE X

Estrogen and Glucose Uptake in Various Brain Regions
Time Course Effects of a 10 μg Dose of $e_2b$ on
4 Hour Glucose Uptake in a Variety of Brain
Regions and the Anterior Pituitary Gland

| BRAIN REGIONS | TIME | | | | |
|---|---|---|---|---|---|
| | 2 HR | 4 HR | 8 HR | 12 HR | 24 HR |
| Medial Basal Hypothalamus | 116 ± 15 | 154 ± 24* | 110 ± 20 | 265 ± 15* | 108 ± 7 |
| Preoptic Area | 132 ± 22* | 221 ± 62* | 80 ± 11 | 67 ± 4* | 98 ± 15 |
| Cerebral Cortex | 76 ± 10* | 98 ± 9 | 120 ± 17 | 215 ± 28* | 100 ± 7 |
| Hippocampus | 132 ± 18* | 125 ± 14* | 71 ± 10* | 88 ± 6 | 93 ± 5 |
| Striatum | 94 ± 30 | 140 ± 17* | 62 ± 9* | 88 ± 6 | 103 ± 7 |
| Cerebellum | 121 ± 29 | 120 ± 14* | 73 ± 9* | 110 ± 62 | 107 ± 9 |
| Brainstem | 111 ± 24 | 90 ± 7 | 70 ± 6 | 118 ± 12 | 94 ± 11 |
| Anterior Pituitary | 95 ± 10 | 220 ± 39* | 142 ± 28 | 66 ± 6* | 125 ± 7* |

*p < 0.05 versus control value within a brain region. Evaluation of the time effect was made with a one-way ANOVA. After analysis and for clarity of presentation data was transformed to percent of mean control.

TABLE XI

Estrogen and Glucose Uptake in Various Brain Region
Dose-Dependent Effects of 4 Hour $E_2B$ Exposure on Glucose Uptake
in a Variety of Brain Regions and the Anterior Pituitary Gland

| BRAIN REGIONS | $E_2B$ DOSE | | |
|---|---|---|---|
| | 1 μg/Kg | 10 μg/Kg | 100 μg/Kg |
| Medial Basal Hypothalamus | 110 ± 23 | 154 ± 24* | 192 ± 28* |
| Preoptic Area | 98 ± 45 | 221 ± 62* | 155 ± 47* |
| Cerebral Cortex | 95 ± 27 | 98 ± 9 | 87 ± 11 |
| Hippocampus | 90 ± 19 | 125 ± 14* | 87 ± 12 |
| Striatum | 111 ± 29 | 140 ± 17* | 74 ± 8* |
| Cerebellum | 112 ± 20 | 120 ± 14* | 57 ± 11* |
| Brainstem | 116 ± 22 | 90 ± 7 | 47 ± 16 |
| Anterior Pituitary | 112 ± 32 | 220 ± 39* | 64 ± 25 |

*p < 0.05 versus control value. Evaluation of the dose effect was accomplished with a one-way ANOVA. Post hoc comparisons were done with a Dunnett's test. After analysis and for clarity of presentation data was transformed to percent of mean control.

TABLE XII

Estrogen and Glucose Uptake in Various Brain Regions
Effect of $E_2B$ on the Extraction of
$C^{14}$-2-Deoxyglucose and $^3H_2O$ in the Brain

| GROUP | $E_2DG$ | $E_{3H2O}$ |
|---|---|---|
| Oil | 0.0803 ± 0.011 | 0.1318 ± 0.943 |
| $E_2B$ | 0.1208 ± 0.013* | 0.1486 ± 0.313 |

*p < 0.05 when compared to oil control. Analyzed with a t-test for independent samples; n = 7, mean ± sem.

We claim:

1. A method for conferring a cytoprotective effect on a population of cells in a male or female subject, comprising:

(a) providing an estrogen compound having insubstantial sex related activity, in a pharmaceutical formulation; and (b) administering the formulation in an effective dose to the population of cells to confer cytoprotection.

2. A method according to claim 1, wherein step (a) further comprises providing an effective dose of the estrogen compound in a pharmaceutical formulation and step (b) further comprises administering the formulation to a subject so as to retard adverse effects of osteoporosis in a male or female subject.

3. A method according to claim 1, wherein the estrogen compound is an alpha isomer.

4. A method according to claim 2, wherein the estrogen compound is an alpha isomer.

5. A method according to claim 3, wherein the estrogen compound is alpha estradiol.

6. A method according to claim 4, wherein the estrogen compound is alpha estradiol.

* * * * *